US011471227B1

(12) United States Patent
Roh et al.

(10) Patent No.: US 11,471,227 B1
(45) Date of Patent: Oct. 18, 2022

(54) APPARATUS, SYSTEM, AND METHOD FOR COMPUTER MODULATED SURGICAL LASER INTENSITY

(71) Applicant: IX Innovation LLC, Seattle, WA (US)

(72) Inventors: Jeffrey Roh, Seattle, WA (US); Justin Esterberg, Mercer Island, WA (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/577,597

(22) Filed: Jan. 18, 2022

(51) Int. Cl.
```
A61B 34/00      (2016.01)
A61B 34/32      (2016.01)
A61B 34/10      (2016.01)
A61B 18/20      (2006.01)
G06N 20/00      (2019.01)
G16H 10/60      (2018.01)
G16H 20/40      (2018.01)
G16H 40/20      (2018.01)
A61B 18/00      (2006.01)
```

(52) U.S. Cl.
CPC .............. *A61B 34/32* (2016.02); *A61B 18/20* (2013.01); *A61B 34/10* (2016.02); *A61B 34/25* (2016.02); *G06N 20/00* (2019.01); *G16H 10/60* (2018.01); *G16H 20/40* (2018.01); *G16H 40/20* (2018.01); *A61B 2018/00541* (2013.01); *A61B 2018/00577* (2013.01); *A61B 2034/101* (2016.02); *A61B 2034/256* (2016.02); *A61B 2034/258* (2016.02)

(58) Field of Classification Search
CPC ......... A61B 34/32; A61B 34/10; A61B 34/25; A61B 18/20; A61B 2034/101; A61B 2034/256; A61B 2034/258; A61B 2018/00541; A61B 2018/00577; G16H 20/40; G16H 40/20; G16H 10/60; G06N 20/00; G61H 20/40; G61H 40/20; G61H 10/60

See application file for complete search history.

(56) References Cited

U.S. PATENT DOCUMENTS

2019/0175272 A1* 6/2019 Khan ..................... A61B 34/32

* cited by examiner

*Primary Examiner* — George Manuel
(74) *Attorney, Agent, or Firm* — Fish & Richardson P.C.

(57) ABSTRACT

A system for performing robotic laser surgery is disclosed. The system comprises at least one surgery equipment, a surgeon terminal, and a communication module. Further, the system includes a surgical computer communicatively coupled to the at least one surgery equipment via the communication module. The surgical computer is configured to transfer data between the surgeon terminal and the at least one surgery equipment. The surgeon terminal is configured to modulate the tunable laser to conduct the surgical procedure in fully autonomous mode or semi-autonomous mode using robot controls. Further, a plurality of sensors is used to real-time data while performing surgical procedure and transmit the real-time data to the surgeon terminal.

24 Claims, 10 Drawing Sheets

| OPERATION DATABASE 118 |||||
|---|---|---|---|---|
| | TIME | TISSUE TYPE | ORIENTATION | PATIENT CONDITION |
| Patient 1 | 2 pm | Cancerous cells | 10cm, 12cm, 09cm | Stable bpm at 80 |
| | 4 pm | Cancerous cells | 10cm, 12cm, 09cm | Increase or Decrease in bpm between 100 to 35 |
| | 5 pm | Cancerous cells | 10cm, 12cm, 09cm | Stabilized bpm to 75 |
| Patient 2 | 2 pm | Cancerous cells | 10cm, 12cm, 09cm | Stable bpm at 80 |
| | 4 pm | Cancerous cells | 10cm, 12cm, 09cm | Increase or Decrease in bpm between 100 to 35 |
| | 6 pm | Cancerous cells | 10cm, 12cm, 09cm | Stabilized bpm to 75 |

FIG. 2

APPARATUS, SYSTEM, AND METHOD FOR COMPUTER MODULATED SURGICAL LASER INTENSITY

TECHNICAL FIELD

This disclosure is generally related to an apparatus, systems, and methods for robotic laser surgery. More particularly, this disclosure is related to techniques for performing tissue ablation based on computer-modulated surgical laser intensity.

BACKGROUND

In oncology surgery, cancer cells can be removed from a tumor bed in a patient. Sometimes, removing the cancer cells can leave behind residual cancer. Residual cancer, which refers to cancer cells left behind after an initial oncology (e.g., resection) surgery, can lead to local recurrence, increased rates of metastasis, and/or poorer outcomes post-surgery. As a result, patients may undergo secondary surgeries after initial oncology surgeries since cancer cells may be found at margins of resected masses during post-operative pathological analysis of the tumor beds. For example, 50% of breast conserving lumpectomies, 35% of limb-sparing sarcoma surgeries, and 37% or radical prostatectomies do not result in complete removal of cancer cells during the initial oncology surgeries.

SUMMARY

The document generally relates to systems, methods, and techniques for adjusting components of a surgical robot used during a surgical procedure to perform the surgical procedure with improved precision. For example, the surgical procedure can be an oncology surgery in which cancer cells are to be removed from a tumor bed in a patient. The surgical robot can include a laser that can be used to remove the cancer cells. The disclosed technology can include a computing system configured to analyze data about the patient and the surgical procedure to determine settings for the laser (e.g., laser intensity). The laser can be adjusted according to the settings. During the surgical procedure, imaging devices and/or sensors can continuously monitor a surgical area of the patient and pass the monitored data to the computing system. The computing system can determine real-time dynamic adjustments that can be made to the laser settings based on the monitoring of the surgical area using the imaging devices and/or sensors. These adjustments can be automatically made to the laser during the surgical procedure to ensure that the procedure is accurately and safely performed and completed. Data collected during the surgical procedure can also be analyzed by the computing system after the procedure to gather additional insight about performing the surgical procedure with precision. The disclosed technology therefore provides intraoperative visualization techniques that can guide a surgeon or other practitioner to better tune a surgical laser to identify and remove cancer cells or other masses/objects accurately and precisely during the surgical procedure.

The disclosed technology provides for performing surgical procedures using a surgical robot having a laser with precisely modulated settings, such as laser frequency, time of exposure, and/or intensity or amplitude of the laser. The laser can be used, for example, to vaporize a specific portion or tissue from a patient's body using the precisely modulated laser frequency as different frequencies of light can have different effects on objects, such as tissues. Surgical procedures that are performed with the surgical robot described herein can also be performed over internal and external tissues of the patient, due to the laser's ability to cut through tissues. Therefore, the disclosed technology can be used for improving a variety of laser-based surgical procedures, such as ablating tissues, removing cancerous cells, treating skin, treating eyes, and/or performing one or more other types of surgical procedures. As an illustrative example, the disclosed technology can be used in dermatology applications. The disclosed technology can be used to scan a patient's body using image data and/or sensor data, as described above. The disclosed technology can then be used to automatically determine normal versus abnormal lesions over the patient's body. Any abnormal lesions identified can then be automatically removed using the surgical robot having the laser. Further, with the introduction of automated surgical procedures, the disclosed technology provides for practitioners to accurately perform the procedures while remote from a surgical site.

Using the disclosed technology, practitioners can readily leverage vast amounts of patient information, resulting in better patient condition diagnoses and assessments to generate improved pre-surgical procedures. The information can be used, for example, to adjust the laser of the surgical robot before and during the surgical procedure. The surgical area of the patient can be continuously monitored during the procedure such that real-time assessments can be made regarding progress of the surgical procedure. Adjustments to settings of the laser, such as laser intensity, position, and orientation, can be dynamically determined and implemented during the surgical procedure to provide for precise and efficient completion of the surgical procedure.

One or more embodiments described herein can include a system for performing autonomous and semi-autonomous surgical procedures with a surgical laser, the system can include a surgical robot that can perform a surgical procedure on a patient and a surgical computing system in communication with the surgical robot. The surgical robot can include a robotic arm, a laser attached to the robotic arm that can emit a surgical laser beam based on one or more laser settings, at least one imaging device that can continuously capture image data of a surgical area of the patient, and at least one sensor that can continuously capture sensor data of at least one of the surgical robot and the patient. The surgical computing system can, before the surgical procedure, retrieve, from a data store, at least one of historic patient data and historic surgical procedure data, determine, based on the retrieved data, a pre-operative plan, and transmit, to the surgical robot, the pre-operative plan. The pre-operative plan can include initial laser settings for the laser and the laser can adjust the one or more laser settings to the initial laser settings in response the surgical robot receiving the pre-operative plan. During the surgical procedure, the surgical computing system can continuously receive, from the at least one imaging device and the at least one sensor, the image data and the sensor data, determine, based on the received data, at least one adjustment to the initial laser settings, and transmit, to the surgical robot, the at least one adjustment to the initial laser settings. The laser automatically can adjust the one or more laser settings based on the at least one adjustment during the surgical procedure.

In some implementations, the embodiments described herein can optionally include one or more of the following features. For example, the surgical computing system can transmit to a user device, for presentation in a graphical user interface (GUI) display, at least one of the pre-operative plan, the initial laser settings, the image data, the sensor data, and the at least one adjustment to the one or more laser settings.

As another example, the surgical computing system can include a base module that can receive an indication from a computing system to prepare the pre-operative plan for the surgical procedure, the computing system being different than the surgical computing system, a pre-operative module that can receive a request from the base module to generate the pre-operative plan, a laser setup module that can (i) receive a request from the base module to generate instructions for causing the laser to automatically adjust the one or more laser settings to the initial laser settings based on the pre-operative plan, and (ii) receive at least one additional request from the base module to generate instructions that cause the laser to automatically adjust the one or more laser settings during the surgical procedure and based on at least one of the image data and the sensor data, an operation module that can receive a request from the base module to cause the surgical robot to perform the surgical procedure based at least in part on the pre-operative plan and at least one of the image data and the sensor data, and an operation close module that can determine that the surgical procedure is complete and generate post-surgical procedure data based at least in part on the pre-operative plan, one or more adjustments that were made to the one or more laser settings during the surgical procedure, and at least one of the image data and the sensor data.

The surgical computing system can also determine the initial laser settings based on polling a data store for configurations of the surgical robot for a same surgical procedure as the surgical procedure, determining an initial position of the robotic arm based on (i) at least one of the configurations of the surgical robot and (ii) the retrieved data, determining workflow parameters for the surgical robot during the surgical procedure based on the retrieved data, and transmitting the initial position of the robotic arm and the workflow parameters to the surgical robot to cause the surgical robot to automatically adjust one or more settings before the surgical procedure.

In some implementations, the surgical computing system can determine, during the surgical procedure, at least one adjustment to the initial laser settings based on identifying a treatment area in the image data based on mapping the surgical area that is captured in the image data, determining a quantity of treated tissue in the identified treatment area, and determining, based on the quantity of treated tissue, the at least one adjustment to the initial laser settings. Moreover, the surgical computing system can determine the at least one adjustment to the initial laser settings based on a determination that the laser is within a threshold distance from a boundary of the identified treatment area. The at least one adjustment can include rotating the laser such that the laser is oriented away from the boundary of the identified treatment area.

The laser settings can include at least one of a laser beam intensity, a size of a beam emitted by the laser, an amount of energy expelled by the laser, a position of the laser relative to the surgical area, and an orientation of the laser relative to the surgical area. Furthermore, the surgical computing system can determine that the surgical procedure is complete based at least in part on the image data and the sensor data. The surgical computing system can determine that the surgical procedure is complete based on identifying a treatment area in the image data based on mapping the surgical area that is captured in the image data, determining a quantity of treated tissue in the identified treatment area, and determining that the quantity of treated tissue exceeds a threshold value.

The surgical computing system can also generate post-surgical procedure data based on applying a machine learning model to at least one of the image data and the sensor data. The machine learning model could have been trained to generate a comparison of monitored surgical procedure data to historic surgical procedure data using a training data set. The monitored surgical procedure data and the historic surgical procedure data can be of a same type of procedure as the surgical procedure. Sometime, the surgical computing system can also generate the post-surgical procedure data based on post-operative feedback received from a user device of a practitioner assigned to the surgical procedure. The surgical computing system can also post the post-surgical procedure data to an electronic health record (EHR) of the patient.

In some implementations, the one or more laser settings can include a laser intensity. The one or more laser settings can include a size of a beam emitted by the laser. The one or more laser settings can also include an amount of energy expelled by the laser. The one or more laser settings can include a position of the laser relative to at least one of the surgical area and a boundary of the surgical area. Moreover, the one or more laser settings can include an orientation of the laser relative to at least one of the surgical area and a boundary of the surgical area.

One or more embodiments described herein can include a surgical laser of a surgical robot that can be used for performing autonomous and semi-autonomous surgical procedures, the surgical laser can be configured to receive, from a surgical computing system in communication with the surgical robot and before a surgical procedure, initial laser settings for the laser, automatically adjust, before the surgical procedure, one or more laser settings to the initial laser settings, perform the surgical procedure based on the adjusted one or more laser settings, receive, from the surgical computing system and during the surgical procedure, at least one adjustment to the initial laser settings, and automatically adjust, during the procedure, the one or more laser settings based on the at least one adjustment received during the surgical procedure. The surgical laser can be attached to a robotic arm of a surgical robot and can be configured to emit a surgical laser beam during the surgical procedure and based on the one or more laser settings. The initial laser settings were determined, by the surgical computing system, as part of a pre-operative plan for the surgical procedure based on at least one of historic patient data and historic surgical procedure data.

In some implementations, the embodiments described herein can optionally include one or more of the following features. For example, the surgical laser can receive the at least one adjustment, from the surgical computing system and during the surgical procedure, based on a determination, by the surgical computing system, that the surgical laser is within a threshold distance from a boundary of a surgical area of a patient during the surgical procedure. The at least one adjustment can include rotating the surgical laser a predetermined amount of degrees such that the surgical laser is oriented away from the boundary of the surgical area.

As another example, the surgical laser can also temporarily stop performing the surgical procedure as the surgical laser automatically adjusts the one or more laser settings and resume performing the surgical procedure once the surgical laser completes automatically adjusting the one or more laser settings.

The devices, system, and techniques described herein may provide one or more of the following advantages. For example, real-time continuous monitoring of the surgical area can provide for real-time adjustments to be dynamically determined and made to the laser used during the procedure. As a result, the laser can accurately and precisely excise tissue or another object from the surgery area and without touching essential structures in the patient's body, such as nerves or blood vessels. Therefore, the disclosed techniques can provide for effective and total resection of tissues or objects, such as cancer cells, in organs.

As another example, the disclosed technology provides a platform for collecting and analyzing an abundance of data to determine accurate patient-specific pre-surgical procedure plans. The disclosed technology can provide a centralized repository for accurate and efficient collection and analysis of patient and surgical procedure data. Tools used in the surgical procedure, such as a laser, can be adjusted based on the pre-surgical procedure plan before the surgical procedure begins. During the surgical procedure, the tools can be continuously adjusted based on real-time monitoring of the patient's surgery area and patient conditions. Dynamically adjusting the tools using a variety of data points from a variety of sources can provide for a patient-specific procedure to be safely and precisely performed.

As another example, the disclosed technology may reduce noise, resolution, and replicability issues that may arise in collecting and analyzing an abundance of data. As a result, the disclosed technology can provide for increased efficiency and accuracy in determining and implementing pre-surgical procedure plans, surgical robot adjustments during the surgical procedure, and analysis of post-surgical procedure data.

Further, the disclosed technology can provide meta-analysis of surgical procedure data to determine more elaborate and precise diagnostic procedures. Therefore, the disclosed technology can provide for more accurate determinations of a type of procedure to perform without having to undergo repetitive and/or invasive diagnostic testing of the patient.

The details of one or more implementations are set forth in the accompanying drawings and the description below. Other features and advantages will be apparent from the description and drawings, and from the claims

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 2 illustrates an example database that can be used with the techniques described herein.

Like reference symbols in the various drawings indicate like elements.

DETAILED DESCRIPTION OF ILLUSTRATIVE EMBODIMENTS

This document generally relates to systems, methods, and techniques for adjusting and continuous monitoring of tools used during surgical procedures, such as lasers. The disclosed technology can provide for determining laser settings before a surgical procedure based on historic patient and/or procedure data. The settings can be applied to the laser. During the surgical procedure, a surgical area of the patient can be continuously monitored to determine additional adjustments to be made to the laser. During the surgical procedure, the additional adjustments can be made to the laser to ensure accurate and precise completion of the surgical procedure.

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise.

Although any systems and methods similar or equivalent to those described herein can be used in the practice or testing of embodiments of the present disclosure, the preferred, systems and methods are now described.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

Figure 1A:
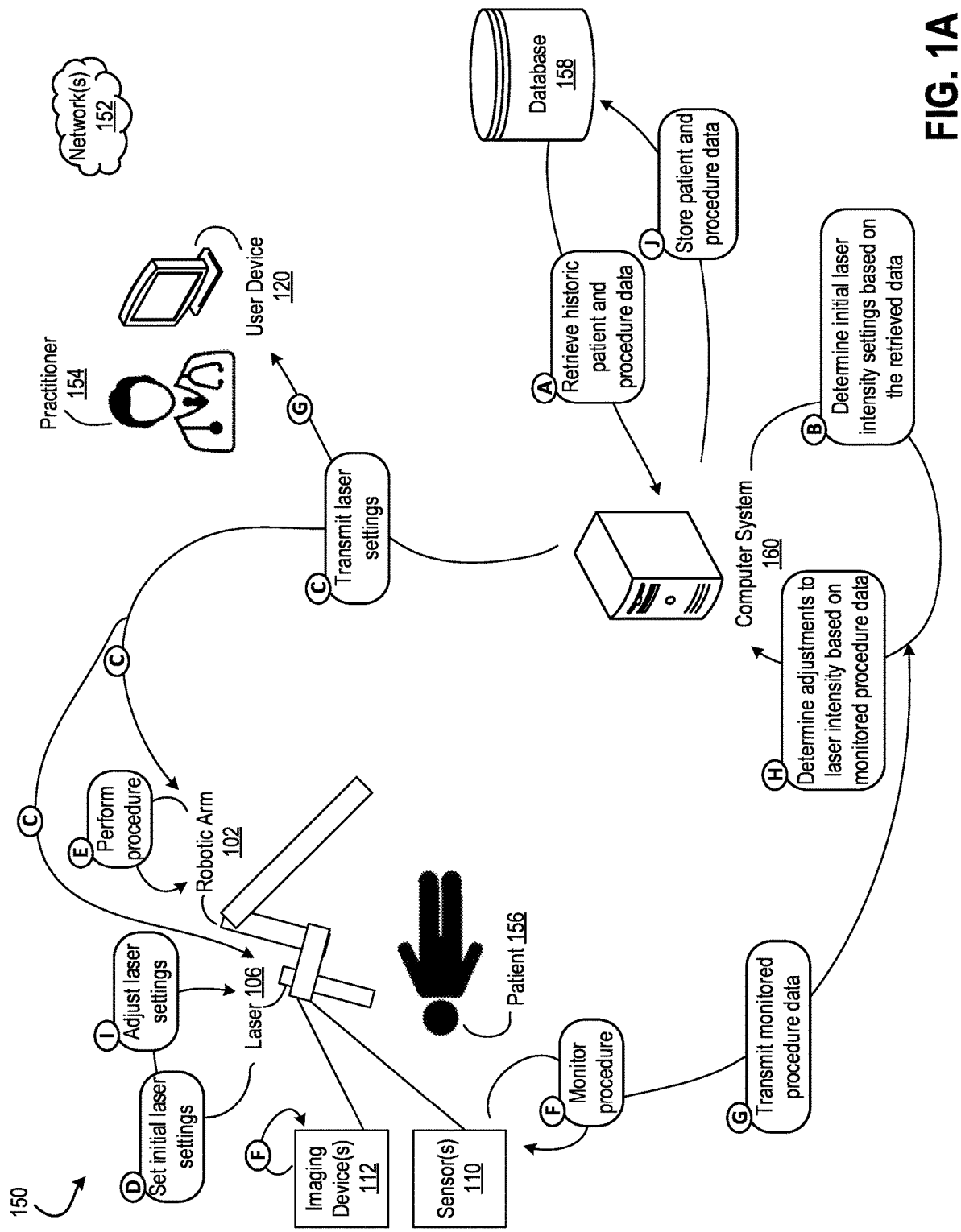
FIG. 1A is a conceptual diagram of a system for performing robotic laser surgery.
Figure 1B:
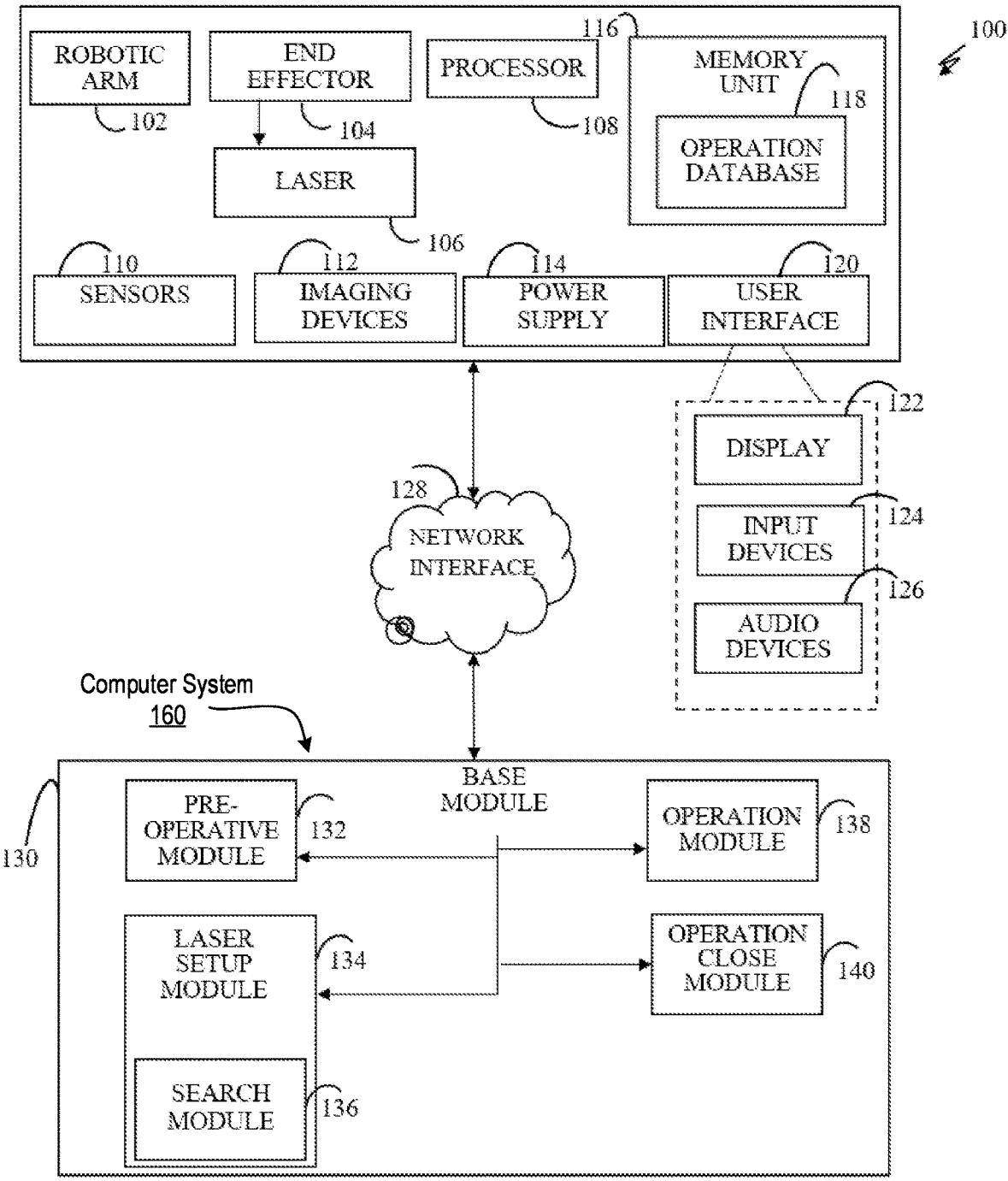
FIG. 1B illustrates a block diagram of one or more system components that can be used for performing robotic laser surgery.

Referring to the figures, FIG. 1A is a conceptual diagram of a system 150 for performing robotic laser surgery. A robotic arm 102 can be used to perform a surgical procedure, as described in below in reference to FIG. 1B. A laser 106 can be connected to and controlled by the robotic arm 102 during the surgical procedure. The robotic arm 102 and the laser 106 can communicate with a computer system 160 via network(s) 152. A user device 120, database 158 (e.g., data store), imaging device(s) 112, and/or sensor(s) 110 can also communicate via the network(s) 152. In some implementations, as shown and described in reference to FIG. 1B, the robotic arm 102, the laser 106, the imaging device(s) 112, and the sensor(s) 110 can be part of a surgical robot (e.g., surgical robot 100 in FIG. 1B). The surgical robot can then communicate with one or more components described herein, such as the computer system 160, in order to perform the surgical procedure. Refer to FIG. 1B for additional discussion about components such as the robotic arm 102, the laser 106, the imaging device(s) 112, the sensor(s) 110, and the user device 120.

The computer system 160 can be any type of computing device, system, network of systems, network of devices, network of computers, cloud-based server, and/or cloud-based system. The computer system 160 can be configured to perform one or more of the techniques described herein, such as determining a pre-surgical procedure plan, determining settings for the laser 106 before the surgical procedure, determining setting adjustments for the laser 106 during the surgical procedure, determining completion status of the surgical procedure, monitoring patient data during the surgical procedure, and performing analysis on post-surgical procedure data.

Still referring to FIG. 1A, the computer system 160 can retrieve historic patient and/or surgical procedure data from the database 158 (block A). The historic data can be retrieved before a surgical procedure. The historic data can include health records about patient 156, information about performing the surgical procedure, information about similar/same surgical procedures that were performed for similar, same, or different patients, etc. The computer system 160 can use the retrieved historic data to determine initial laser intensity settings (block B). The initial laser intensity settings can include but are not limited to a size of a beam that should be emitted by the laser 106, an amount of energy that should be expelled by the laser 106 beam, a position of the laser 106, and/or an orientation of the laser 106. The computer system 160 can then transmit the initial laser intensity settings to the robotic arm 102, the laser 106, and/or the user device 120 (block C).

The laser 106 can then set the laser 106 to the initial laser intensity settings (block D). In some implementations, the robotic arm 102 can receive the laser settings (block C) and transmit the settings to the laser 106 to cause the laser 106 to adjust its intensity to the laser intensity settings (block D). In some implementations, the user device 120 can receive the laser intensity settings (block C) and present the settings to a practitioner 154 (e.g., surgeon) in a graphical user interface (GUI) display at the user device 120. The practitioner 154 can be located at a site, such as a hospital, where the surgical procedure is being performed on the patient 156. The practitioner 154 may also be remote from the site where the surgical procedure is being performed. Regardless of a physical location of the practitioner 154, the practitioner 154 can review the initial laser settings at the user device 120. The practitioner 154 can also monitor performance of the surgical procedure by the robotic arm 102 from the user device 120. For example, the practitioner 154 can make adjustments to one or more laser intensity settings at the user device 120 and during the surgical procedure based at least in part on monitored patient data from the imaging device(s) 112 and/or the sensor(s) 110. Adjustments made by the practitioner 154 at the user device 120 can then be transmitted to the robotic arm 102 and/or the laser 106. The laser 106 can automatically implement the practitioner-generated adjustments during the surgical procedure.

Still referring to FIG. 1A, once the laser 106 sets the initial laser intensity settings (block D), the robotic arm 102 can begin performing the surgical procedure (block E). As described herein, the practitioner 154 can monitor and/or control the robotic arm 102 during the procedure from the user device 120.

As the surgical procedure is being performed, the imaging device(s) 112 and/or the sensor(s) 110 can continuously monitor the procedure (block F). For example, the imaging device(s) 112 can capture image data of a surgical area of the patient 156. Intraoperative computed tomography (CT) scanning can be used during the procedure to identify how much bone resected before and after the procedure. Fluoroscopy (e.g., a continuous X-ray beam that passes through a body part, organ, or other object in the patient 156) can be used to determine whether an implant is placed and whether or not anatomy of the patient 156 has changed as a result of the implant insertion. Moreover, intraoperative cameras capture image data before and after the procedure, which can be used by the computer system 160 to determine whether the procedure has been performed properly (for example, to determine whether a skin legion has been resected properly for a dermatological laser procedure). In block F, the sensor(s) 110 can capture data about the patient 156, such as body temperature, heartrate, respiration/breathing rate, etc. The sensor(s) 110 can also capture data about the laser 106 and/or the robotic arm 102, such as a laser intensity, a speed of the robotic arm 102, and/or a torque of the robotic arm 102.

Monitored procedure data can then be transmitted to the computer system 160 (block G). In some implementations, the monitored procedure data can also be transmitted to the user device 120 to be viewed by the practitioner (block G). The monitored procedure data can be transmitted directly from the imaging device(s) 112 and/or the sensor(s) 110 to the user device 120. The monitored procedure data can also be transmitted from the computer system 160 to the user device 120. For example, the computer system 160 can process the monitored procedure data and generate human-readable output including the monitored procedure data to be presented in user-friendly interfaces at the user device 120.

The computer system 160 can determine adjustments to the laser 106 intensity settings based on the monitored procedure data (block H). As an illustrative example, adjustments to an orientation and/or position of the laser 106 can be determined to ensure that the laser 106 precisely removes particular tissues in the patient 156's body without interacting with or otherwise contacting essential structures, such as nerves and vessels in the patient 156's body. As another illustrative example, the computer system 160 can determine one or more other laser intensity setting adjustments based on the patient 156's heartrate slowing or dropped below a threshold range, their body temperature dropping below a threshold range, their respiration rate dropping below a threshold range, a speed of the robotic arm 102 exceeding a threshold speed, a laser intensity exceeding a threshold intensity for the particular surgical area, etc. Any of the threshold ranges described herein can be specific to the particular patient 156 or a population of users sharing common characteristics, such as age, gender, and/or type of procedure. The threshold ranges can be determined by the computer system 160 and based on the retrieved historic patient and/or procedure data (block A).

During the procedure and in real-time, any adjustments that are determined by the computer system 160 in block H can be transmitted to at least the laser 106 (block C). The laser 106 can adjust the laser settings accordingly (block I) and the robotic arm 102 can continue to perform the procedure (block E). As the procedure continues to be performed, the imaging device(s) 112 and/or the sensor(s) 110 can monitor the surgical procedure (block F) and provide the monitored procedure data to at least the computer system 160 (block G) so that the computer system 160 can determine any additional adjustments to the laser intensity settings (block H). Blocks A-H can be continuously performed for a duration of the surgical procedure. Therefore, the disclosed techniques provide for continuously monitoring and adjusting the laser 106 so that the surgical procedure can be performed with accuracy and precision while also maintaining the safety and health of the patient 156.

Moreover, the computer system 160 can also store patient and procedure data in the database 158 (block J). The computer system 160 can store the patient and procedure data in the same database as the database from which the computer system 160 retrieves the historic data in block A. In some implementations, the computer system 160 can store the patient and procedure data in a data store that is different than the database from which the computer system 160 retrieves the historic patient and procedure data in block A. The computer system 160 can store the monitored procedure data in the database 158 (block J). Sometimes, as the computer system 160 receives the monitored procedure data, it can store the data in the database 158. In some implementations, the computer system 160 can store the monitored procedure data in the database 158 once the surgical procedure is completed. In yet some implementations, the computer system 160 may store only some of the monitored procedure data. Sometimes, the computer system 160 may perform analysis on the monitored procedure data after the surgical procedure is completed and then store resulting data from the analysis in the database 158. The data stored in the database 158 can then be used by the computer system 160 to determine initial laser intensity settings in subsequent surgical procedures (for the patient 156 or for different patients). The data stored in the database 158 can also be added or posted to electronic health records (EHRs) of the patient 156. Moreover, the data stored in the database 158 can be used in subsequent analysis of the patient 156 and/or the surgical procedure.

FIG. 1B illustrates a block diagram of one or more system components that can be used for performing robotic laser surgery. More particularly, FIG. 1B illustrates a surgical robot 100 for robotic laser surgery, as described throughout this disclosure. The surgical robot 100 may include the robotic arm 102 (e.g., refer to FIG. 1A) and an end effector 104. The surgical robot 100 may be used for carrying out desired effects or performing a surgery, surgical procedure, or other type of operation.

The robotic arm 102 can be a type of mechanical arm, which can be programed, to perform a surgical procedure with precision, flexibility, and control. The robotic arm 102 may be a sum of the mechanism or may be part of a more complex robot. As non-limiting examples, the robotic arm 102 can be a Cartesian robot, a collaborative robot, an anthropomorphic robot, a SCARA robot, a spherical/polar robot, an articulated robot, and/or a parallel robot. One or more other robotic components are also possible. The robotic arm 102 can be used to guide the laser 106 to facilitate desired actions and/or perform the surgical procedure. For example, the robotic arm 10 can guide the laser 106 to ablate tissues or cancer cells from a particular area/region of a patient's body.

In some implementations, the robotic arm 102 can be a serial robotic arm having a chain of links that can be moved by joints. The joints can be actuated by motors. The robotic arm 102 may also be classified in terms of a number of degrees of freedom. For example, the number of degrees of freedom can be equal to a number of joints that move the links of the robotic arm 102. Sometimes, at least six degrees (e.g., 6°) of freedom may be required to enable the robotic arm 102 to reach an arbitrary pose (e.g., position and/or orientation) in three dimensional space (e.g., 3D space). Additional degrees of freedom can be used to allow a change in configuration of the links of the robotic arm 102. The configuration of the robotic arm 102 may therefore be calculated by a mathematical process called inverse kinematics, in terms of joint angles, and given a desired pose of the robot arm 102 in three dimensional space.

The end effector 104 can include the laser 106 described in FIG. 1A. The end effector 104 may include, but is not limited to, a tunable laser that can be used in a variety of surgical procedures and other types of operations. As an illustrative example, the end effector 104 can include a tunable laser for ablating tissues using laser rays that are emitted at different intensities. In some implementations, the end effector 104 may be, but is not limited to, a surgical tool, such as a drill, forceps, scalpel, retractor, dilator, grasper, gripping device, probe, endoscope, or other key segments.

As a surgical tool, the end effector 104 can allow for performance of specific actions and/or carrying out of desired effects during the surgical procedure, including but not limited to modifying biological tissue and/or providing access for viewing the biological tissue. As a gripping device, the end effector 104 can allow the robotic arm 102 to pick up and hold objects, and enable manufacturers to automate key processes during surgical procedures. As a probe, the end effector 104 can include a switch that can be used to trigger and make contact with a surface, such as external tissue of the patient's body. As a scalpel, the end effector 104 can include a small and sharp-bladed instrument that can facilitate the robotic arm 102 to cut into tissue or other objects during the surgical procedure. Accordingly, the end effector 104 can vary depending on a type of surgical procedure to be performed with the surgical robot 100. Furthermore, the end effector 104 can be a peripheral device that attaches to the robotic arm 102, thereby allowing the robotic arm 102 to interact with one or more other components described herein.

Further, the surgical robot 100 can include a processor 108 for controlling functions of the surgical robot 100. The surgical robot 100 can also include sensor(s) 110 that can be configured to sense/detect information/data related to the at least one surgical robot 100 being used during the surgical procedure in an operating room (OR). In some implementations, multiple sensors 110 can be used. The sensors 110 can measure a variety of parameters related to the at least one surgical robot 100, including, but not limited to, speed of the robotic arm 102, torque of the robotic arm 102, temperature of the surgical robot 100, power status of the surgical robot 100, intensity of the laser 106 being diverted onto a surgical area of the patient from the end effector 104, etc. The sensors 110 generally can include, but are not limited to, GPS, infrared cameras, wireless communication relay devices, lasers, etc.

The sensors 110 may also include thermal and/or infrared sensors that can continuously detect temperature and intensity of laser beams imparting over the surgical area(s) (e.g., ablated area(s)) of the patient. In some implementations, the sensors 110 may include patient monitoring sensors, including but not limited to sensors that monitor heartrate, blood pressure, and blood oxygen concentration of the patient.

Further, the surgical robot 100 can include one or more imaging devices 112. The imaging devices 112 can be used to capture image data of the patient's body during the surgical procedure. The imaging devices 112 can include cameras, X-ray machines, and/or other imaging mechanisms. The imaging devices 112 can continuously capture image data of the particular surgical area during the surgical procedure. Therefore, the imaging devices 112 can be trained on the particular surgical area. In some implementations, the imaging devices 112 may also capture image data of portions of the OR that may include the robotic arm 102. As a result, the image data of the robotic arm 102 can be processed and used by the computer system 160 described herein to determine whether any adjustments can or should be made to the surgical robot 100 during the surgical procedure.

The surgical robot 100 may also include a power supply 114. The power supply 114 may drive various hardware units and components of the surgical robot 100 by providing power to such hardware units and components. The power supply 114 can be an internal power source to the surgical robot 100. Sometimes, the power supply 114 can be an external power source to the surgical robot 100. In some implementations, the power supply 114 can be a battery. The battery may be a Lithium polymer battery (Li—Po), due to its lightweight, high discharge rate, and capacity.

Further, the surgical robot 100 can include a memory unit 116. The memory unit 116 can include short-term volatile memory and/or long-term persistent memory. The memory unit 116 can also include an operation database 118. In some implementations, the operation database 118 can be the same as the database 158 described in FIG. 1A. In some implementations, the operation database 118 can be different from the database 158. Moreover, in some implementations, the memory unit 116 can be in communication (e.g., via the network interface 128 and/or the network(s) 152) with the operation database 118. The operation database 118 can then be a remote data store and/or a cloud-based data store. The operation database 118 may store a flow of operation for the surgical procedure. The operation database 118 is described further below in FIG. 2.

The surgical robot 100 may also include the user interface 120 (e.g., user device) for displaying controls and other information/parameters/data related to the surgical procedure. The user interface 120 may include a display 122, input devices 124, and audio devices 126. The display 122 may facilitate a method for viewing, by the practitioner or another relevant user, information before, during, and after the surgical procedure. The input devices 124 may include, but are not limited to, a mouse, keyboard, microphone, joystick, and/or a handheld controller. The audio devices 126 may include speakers and microphones for interacting with the surgical robot 100. In some implementations, the user interface 120 may include imaging device outputs. The practitioner can use the audio devices 126 and/or the input devices 124 to control aspects of the surgical robot 100. The practitioner may also view real-time data that is monitored by the imaging devices 112 and/or the sensors 110 and presented at the display 122 to determine one or more adjustments or controls to make to components of the surgical robot 100 during the surgical procedure.

Still referring to FIG. 1B, the surgical robot 100 can also include a network interface 128 that provides communication between the components of the surgical robot 100 and/or the computer system 160. For example, the imaging devices 112 may include optical sensors that continuously capture image data of a site of the surgical procedure. The imaging devices 112 can transmit the image data to the robotic arm 102 and/or the process 108 via the network interface 128. The processor 108 may be referred to as a controller to control operation of the sensors 110, the imaging devices 112, the robotic arm 102, the end effector 104, and/or the laser 104. Controls and data can be transmitted from the processor 108 to the user interface 120 via the network interface 128.

The network interface 128 may be communicatively coupled to the robotic arm 102, the end effector 104, the laser 106, the processor 108, the memory unit 116, the sensors 110, the imaging devices 112, the power supply 114, and/or the user interface 120 for real-time assistance and monitoring in the OR. The network interface 128 may also be synchronized with the operation database 118 to transmit information for storage. Moreover, the network interface 128 can provide communication between the surgical robot 100 and a base module 130 of the computer system 160.

The network interface 128 may also communicate with a cloud network to be implemented using a collection of server devices that can provide one or more services to coupled devices and data sources. Sometimes, the network interface 128 may be a wired and/or a wireless network (e.g., the network(s) 152 in FIG. 1A). The network interface 128, if wireless, may be implemented using communication techniques such as Visible Light Communication (VLC), Worldwide Interoperability for Microwave Access (WiMAX), Long Term Evolution (LTE), Wireless Local Area Network (WLAN), Infrared (IR) communication, Public Switched Telephone Network (PSTN), Radio waves, and other communication techniques, known in the art. The network interface 128 may allow ubiquitous access to shared pools of configurable resources and higher-level services that can be rapidly provisioned with minimal management effort, often over the internet. The network interface 128 can rely on sharing of resources to achieve coherence and economies of scale, such as a public utility, while third-party clouds can enable organizations, such as hospitals and ORs, to focus on their surgical tasks instead of expending resources on computer infrastructure and maintenance.

Still referring to FIG. 1B, the computer system 160 can be configured to perform one or more techniques described herein, such as preparing components of the surgical robot 100 for the surgical procedure, continuously monitoring the surgical robot 100 during the procedure, determining adjustments to components of the surgical robot 100 during the procedure, determining when to complete and close the procedure, and post-surgical procedure processing and analysis of data that was collected during the procedure. The computer system 160 can be a cloud-based server and/or system, a network of computing devices and/or systems, and/or a computer/device. The computer system 160 can execute multiple services, or micro services, to perform the techniques described herein. In some implementations, the computer system 160 can include sub computing systems to perform each of the techniques described herein.

The computer system 160 can include the base module 130, a pre-operative module 132, a laser set up module 134, a search module 136, an operation module 138, and an operation close module 140. Each of the modules 130, 132, 134, 136, 138, and 140 can be executed by a separate computing system, device, and/or engine. In some implementations, the modules 130, 132, 134, 136, 138, and 140 can be services, or micro services, that are executed by the computer system 160.

Figure 3A:
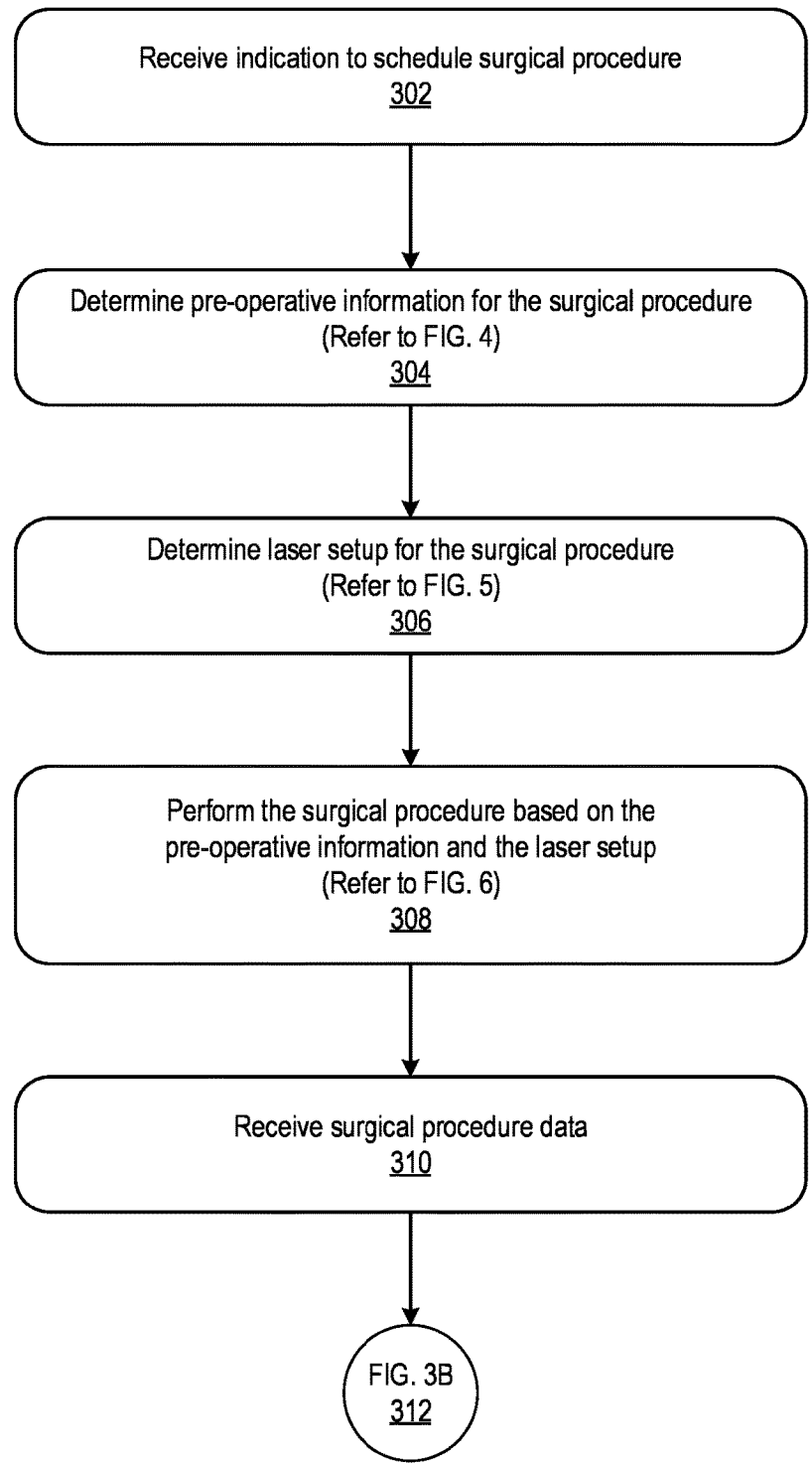
FIGS. 3A-B are a flowchart of a process for performing robotic laser surgery.
Figure 3B:
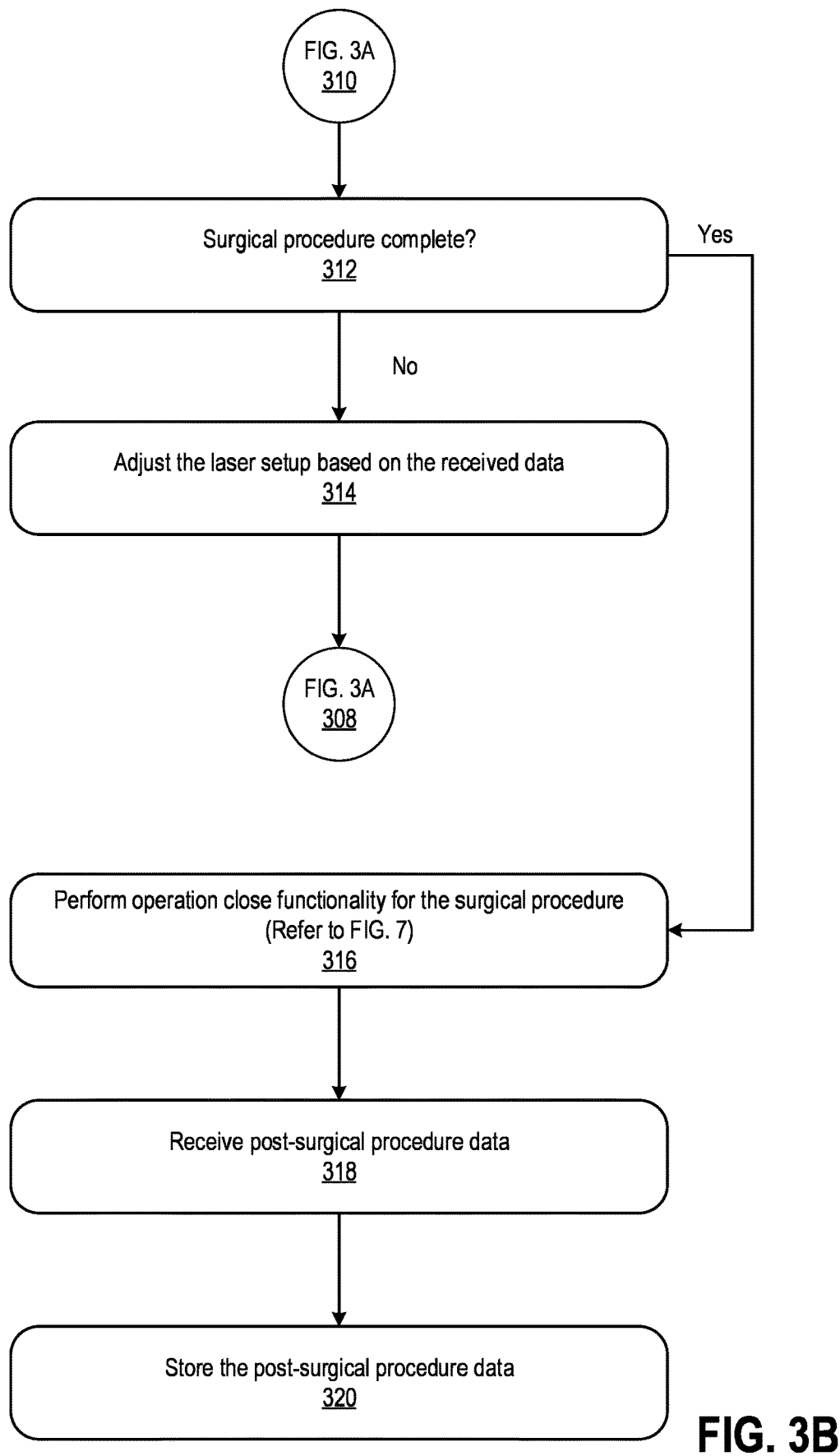

Referring to the modules of the computer system 160, the base module 130 can be configured to retrieve information related to the surgical procedure, from the operation database 118. The base module 130 can therefore be used to prepare for the surgical procedure. The base module 130 may be further described as shown in FIGS. 3A-B.

The pre-operative module 132 can be part of the base module 130 and configured to determine which type of surgical procedure to be performed. This determination can be made using the information that is retrieved by the base module 130. For example, the pre-operative module 132 can determine that scar tissue is to be removed from a particular patient's body. The pre-operative module 132 can also determine and provide a pre-operative plan for the surgical procedure as described further below in reference to FIG. 4.

The laser setup module 134 can also be part of the base module 130 and configured to set up the at least one surgical robot 100 according to the pre-operative plan from the pre-operative module 132. The laser setup module 134 can first poll the operation database 118 for types of tissues, no-fly zones, or areas where lower laser intensity may be required for the particular surgical procedure and/or for the particular patient's condition(s). The types of tissues may be, but are not limited to, internal and external tissues. The no-fly zones may be non-ablation areas, such as sensitive tissues that can include nervous tissue or vital organs. The laser setup module 134 may also include a variety of configuration settings. The laser setup module 134 may configure a position of the surgical robot 100 and determine at which direction the robotic arm 102 and the end effector 104 with the tunable laser 106 should point based on analysis of the image data received from the imaging devices 112. Therefore, the laser setup module 134 can receive the image data and process the image data to make adjustments to settings of components of the surgical robot, such as the robotic arm 102, the end effector 104, and the laser 106. The laser setup module 134 may also retrieve preferred workflow parameters from the operation database 118 for the particular surgical procedure and/or the particular patient. For example, a laser robotic surgery can be conducted on a patient to remove scar tissue from lungs. The search module 136 of the laser setup module 134 may retrieve orientation information for the robotic arm 102 for this particular type of surgery. The retrieved information can indicate that the robotic arm 102 should be kept 30 degrees inclined so that the tissue can be accurately removed. The retrieved information can also indicate that the laser intensity should be kept between 10-20 W/cm$^2$.

The operation module 138 can also be part of the base module 130 and configured to start the surgical procedure with respect to the configuration settings provided by the laser setup module 134. The operation module 138 may perform one or more steps that are determined by components of the computer system 160 and/or the practitioner at the user interface 120 during the surgical procedure. The operation module 138 is further described in conjunction with FIG. 6. In some implementations, the operation module 138 may also control the imaging devices 112 to capture image data of the surgical area during the surgical procedure.

The operation close module 140 can also be part of the base module 130 and configured to analyze optical information related to the surgical procedure that is being conducted. For example, the operation close module 140 can receive monitored data from the imaging devices 112 and/or the sensors 110. During the procedure, the operation close module 140 can process and analyze this data to determine whether the surgical procedure is near completion or is complete. After the procedure, the operation close module 140 can analyze this data to determine effectiveness of the adjustments and controls that were made/performed during the surgical procedure.

In some implementations, the operation close module 140 may conduct a post-operative interview/review from the practitioner regarding accuracy of tissue being ablated and risk associated with the surgical procedure, such as complication during the removal of scar tissue. Further, the operation close module 140 can analyze the optical information using machine learning algorithms, models, and/or techniques to assess surgical procedures and compare them to data about previous surgical procedures that are stored in the operation database 118. The operation close module 140 may determiner, from the optical information, an amount of healthy tissue being removed during the surgical procedure compared to the previous surgical procedures, which can be beneficial to fine tune settings, controls, and other adjustments that can be made to components of the surgical robot 100 during subsequent similar/same surgical procedures.

In some implementations, the operation close module 140 may also analyze a duration during which the practitioner was offline or off the mark during the surgical procedure. Such an analysis can be beneficial to determine effectiveness and role of the practitioner in the surgical procedure. This analysis can also be beneficial to rate or otherwise assess the practitioner's skills, especially when this analysis is combined with analysis of data about previous surgical procedures that the practitioner performed (the data being stored in the operation database 118). Moreover, the operation close module 140 may send information related to the surgical procedure and the practitioner's feedback/review/rating(s) to an electronic health record (EHR) for the patient that underwent the surgical procedure. The operation close module 140 is further described in conjunction with FIG. 7.

FIG. 2 illustrates an example database that can be used with the techniques described herein. More particularly, FIG. 2 depicts example data entries in the operation database 118. The operation database 118 may be configured to store feedback from the practitioner about how the surgical procedure was performed and risks associated with each step that was taken during the surgical procedure. In some implementations, the sensors 110 can detect speech from the practitioner and provide the detected speech to the processor 108 of the surgical robot 100 or the computer system 160 for further processing. The detected speech can be converted into text format and stored in the operation database 118. The operation database 118 can store one or more other data that is detected by the sensors 110 and/or captured by the imaging devices 112. This data can be stored and retrieved (e.g. by the computer system 160) at another time to perform calculations and generate recommendations for performing and completing the surgical procedure.

The operation database 118 can also be configured to store parameters that are related to the surgical robot 100 and/or parameters for the surgical robot 100 that were used during the surgical procedure. The operation database 118 may also store parameters for different types of surgical procedures. The parameters may include, but are not limited to, a laser wavelength, input power supplied to the surgical robot 100, duty cycle, etc. Furthermore, the operation database 118 may also store data about a variety of types of operation lasers that can be employed during the surgical procedure. The operation database 118 can maintain a library of workflows, operations, and disease states to treat using the different types of operation lasers and parameters of the surgical robot 100. The library of workflows may include different surgical procedures that may be performed to treat a specific disease, such as ablation of scar tissue, removal of cancerous cells, etc.

In some implementations, the operation database 118 can store information related to ablated areas (or other surgical areas) in the patient's body where the surgical robot 100 may perform or already performed the surgical procedure. The ablated areas may include internal tissues and/or external skin of the patient. For example, the operation database 118 may store which area(s) of the patient's body is to be treated such as, but not limited to, skin, muscle tissue, fat cells, cancerous tissues, scar tissues, etc. Further, the operation database 118 may be configured to store information related to the patient's health records. For example, the health records may include previous treatments, if any, that were done on the patient. The operation database 118 may store information related to, such as, but not limited to, types of cells previously ablated and/or tissues being removed. The operation database 118 may also store information related to pervious surgical procedures such as previous real-time operation data, which can then be utilized during an on-going surgical procedure by the computer system 160 described herein.

Data stored in the operation database 118 can be useful to set-up the surgical robot 100 according to the patient's health records and particular health conditions/state. For example, as shown in FIG. 2, the operation database 118 can store information related to patient 1 at time 2 pm, orientation of the surgical robot 100 at 10 cm, 12 cm, 09 cm for cancerous tissues, and a stable bpm at 80; at 4 pm, orientation of the surgical robot 100 at 10 cm, 12 cm, 09 cm for cancerous tissues, and an increase or decrease in bpm between 100 to 35; and at 5 pm, orientation of the surgical robot 100 at 10 cm, 12 cm, 09 cm for cancerous tissues, and a stable bpm at 75.

The operation database 118 may store parameters of the surgical robot 100 while performing the surgical procedure. For example, the parameters while performing the surgical procedure may include, but are not limited to, size of the surgical robot 100 or the robotic arm 102, orientation of the robotic arm 102, etc.

FIGS. 3A-B are a flowchart of a process 300 for performing robotic laser surgery. The process 300 can also be used to perform any other type of procedure that can use the surgical robot 100 described herein. The process 300 can be performed by the computer system 160 described in reference to FIGS. 1A-B. In some implementations, one or more blocks of the process 300 can be performed by one or more of the modules 130, 132, 134, 136, 138, and 140 described in reference to FIG. 1B. The process 300 can also be performed by one or more other computing systems, devices, computers, networks, cloud-based systems, and/or cloud-based services. For illustrative purposes, the process 300 is described from the perspective of a computer system.

FIGS. 3A-B are explained in conjunction with FIGS. 1-2 and 4-7. In some alternative implementations, one or more blocks depicted and described in FIGS. 3-7 may occur in one or more different orders. For example, blocks shown in succession in FIGS. 3A-B may be executed substantially concurrently or one or more blocks may sometimes be executed in a reverse order, depending upon functionality involved.

Referring to the process 300 in both FIGS. 3A-B, the computer system may receive an indication to schedule a surgical procedure (block 302). For example, the base module 130 at the computer system 160 can receive a request from a surgical site (e.g., an operation room) to schedule the surgical procedure. Sometimes, the base module 130 may receive the request from the surgical site, which may be either at a remote location from the operating room or within the operating room. For example, a patient Alex can be diagnosed with lung cancer at a surgical facility in New York, USA, and may need robotic laser surgery to remove cancerous cells from his lungs. The surgical procedure can be conducted by Dr. Van, who performs the surgery from a location outside the operating room of the surgical facility. Accordingly, the base module 130 can receive the request from the surgical facility in New York to schedule the robotic laser surgery for Alex.

In block 304, the computer system can determine pre-operative information for the surgical procedure. The base module 130, for example, may trigger the pre-operative module 132. Block 304 is further described in FIG. 4.

Next, in block 306, the computer system can determine a laser setup for the surgical procedure. For example, the base module 130 may be configured to trigger the laser setup module 134. The laser setup module 134 may also be configured to set the at least one surgical robot 100 according to the pre-operative plan of the pre-operative module 132 in block 306. Sometimes, setting the at least one surgical robot 100 can be performed in block 308, described below. Block 306 is described in further detail in FIG. 5.

The computer system can perform the surgical procedure based on the pre-operative information and the laser setup in block 308. For example, the base module 130 can receive an acknowledgement from the laser setup module 134 that the laser has been set up for the surgical procedure. The surgical procedure can now be performed. As another example, the base module 130 may receive preferred/selected workflow parameters from the laser setup module 134 for removal of cancerous cells from the lungs of example patient Alex. The parameters can include settings such as adjusting laser intensity between 0-15 $W/cm^2$ and inclining the surgical robot 100 at 30 degrees northwards while performing surgical procedure (or while starting the surgical procedure). The base module 130 may trigger the operation module 138 in block 308. The operation module 138 can adjust initial settings of the surgical robot 100 using the received parameters before beginning the surgical procedure. Block 308 is described in further detail in FIG. 6.

The computer system can continuously receive surgical procedure data in block 310. For example, the base module 130 may be configured to receive the surgical procedure data from the operation module 138. The operation module 138 can receive the data from the imaging devices 112 and/or the sensors 110 during the surgical procedure.

Using the surgical procedure data, the computer system can determine whether the surgical procedure is complete in block 312. For example, the computer system can process the image data to determine what portions of a surgical area have been ablated/removed. The computer system can determine a percentage of contacted surgical area and whether that percentage exceeds some threshold range/value. If the percentage exceeds the threshold range/value, the computer system can determine that the surgical procedure is complete (e.g., 100% of Alex's lung tissue having the cancer cells has been removed).

If the computer system determines that the surgical procedure is complete in block 312, the computer system can proceed to block 316, described further below. If the computer system determines that the surgical procedure is not complete, then the computer system can proceed to block 314, in which the computer system can adjust the laser setup (or other settings of the surgical robot 100) based on the received data. For example, the operation module 138 can determine and adjust the laser intensity of the tunable laser 106 from 15-0 W/cm² so that 99.8% of cancerous cells are removed and only 0.02% of non-cancerous cells are removed. As a result, accuracy and precision of the laser 106 can be improved during the surgical procedure.

Once the laser settings are adjusted, the computer system can return to block 308, in which the surgical procedure is performed with the adjusted laser settings. Blocks 308-310 can be continuously performed until the computer system determines that the surgical procedure is complete in block 312.

Referring to block 316, the computer system can perform operation close functionality for the surgical procedure. For example, the base module 130 may trigger the operation close module 140. Block 316 is described in further detail in FIG. 7.

The computer system can also receive post-surgical procedure data in block 318. As described above, the data can include feedback from the practitioner who performed the surgical procedure with the surgical robot 100. The data can also be determined by the operation close module 140 as described in FIG. 7 based on analysis of data that was continuously monitored during the surgical procedure.

The computer system can store the post-surgical procedure data in block 320. This data can be stored in the database 158 and/or the database 118 described throughout this disclosure. This data can be stored in relation to the particular patient who underwent the surgical procedure. Thus, this data can be added to EHRs of the patient. This data can also be stored in relation to the type of surgical procedure that was performed. Thus, this data can be used for preparing and preparing future similar/same surgical procedures for one or more patients.

Figure 4:
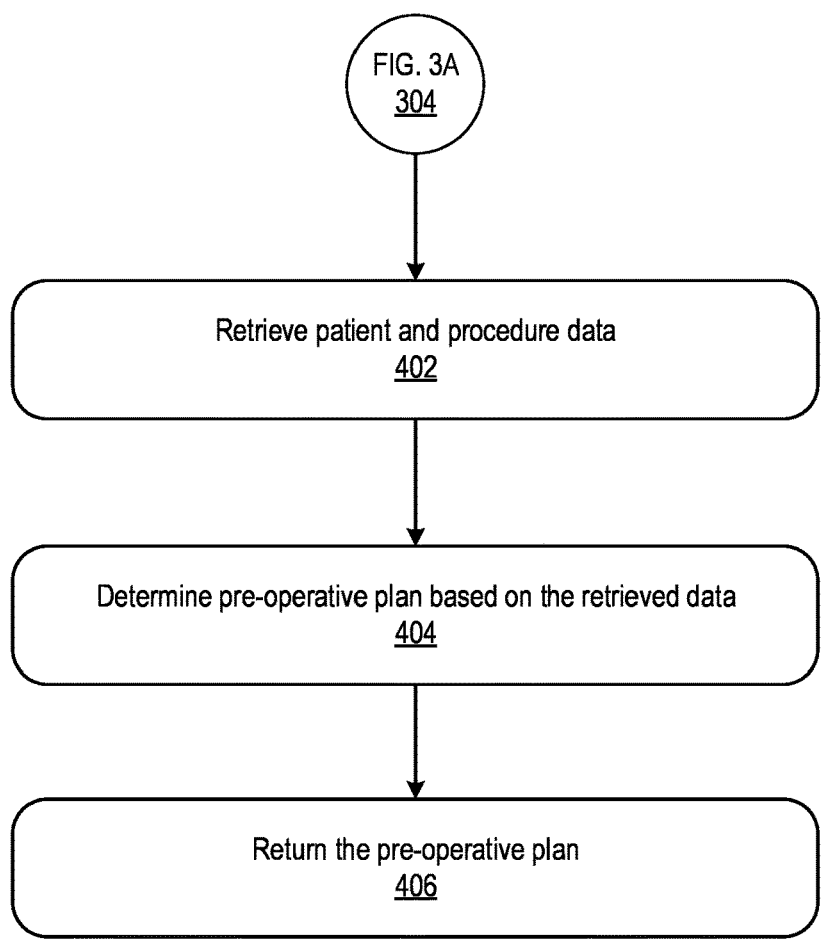
FIG. 4 is a flowchart of a process for determining pre-operative information for a robotic laser surgery.

FIG. 4 is a flowchart of a process 400 for determining pre-operative information for a robotic laser surgery. The process 400 can also be used to perform any other type of procedure that can use the surgical robot 100 described herein. The process 400 can be performed by the computer system 160 described in reference to FIGS. 1A-B. In some implementations, one or more blocks of the process 400 can be performed by one or more of the modules 130, 132, 134, 136, 138, and 140 described in reference to FIG. 1B. The process 400 can also be performed by one or more other computing systems, devices, computers, networks, cloud-based systems, and/or cloud-based services. For illustrative purposes, the process 400 is described from the perspective of a computer system.

Referring to the process 400 in FIG. 4, the computer system can retrieve patient and procedure data form a data base in block 402. The data can be retrieved from the database 158 and/or the database 118 describe above. For example, the pre-operative module 132 of the computer system 160 may receive a prompt from the base module 130 to begin preparing for the surgical procedure (block 304 in FIG. 3A). The prompt can indicate that the surgical procedure is to be performed at some future time. In some implementations, the pre-operative module 132 may determine which type of surgical procedure to perform. Further, the pre-operative module 132 may retrieve information related to previous treatments of the patient from the operation database 118 and/or the database 158.

Example patient Alex might have gone through a surgery for thyroid a year ago. Information about this procedure can be retrieved in block 402 and used to more accurately determine settings for performing the upcoming surgical procedure for Alex, regardless of whether the upcoming surgical procedure is also for the thyroid.

The computer system can determine a pre-operative plan based on the retrieved data in block 404. For example, the pre-operative module 132 may prepare the pre-operative plan for the patient. The pre-operative module 132 may consider previous treatments and/or surgical procedures of the patient to prepare the pre-operative plan. For example patient Alex, the pre-operative module 132 can take into account the previous surgery related to thyroid while preparing a pre-operative plan by removing use of drugs to which a patient with thyroid may be sensitive. The pre-operative plan can also be determined based on data and/or parameters specific to the particular type of surgical procedure to be performed, the type of surgical robot 100 and components therein that will be used during the surgical procedure, and other health data related to the patient.

The computer system can return the pre-operative plan in block 406. For example, the pre-operative module 132 can prepare the pre-operative plan for performing the robotic laser surgery to remove cancerous cells from the lungs of example patient Alex, by retrieving information related to the previous treatments of Alex from the operation database 118. The pre-operative module 132 may set up a plan for the treatment of the cancerous cells with respect to the previous treatments done for Alex. For example, two years back, Alex had undergone a surgery for the treatment of spine, the pre-operative module 132 can set up the pre-operative plan such that Dr. Van can be informed about the previous spinal surgery and treatment so as to not affect Alex's spinal condition during the following procedure. This information in the pre-operative plan can be returned and/or transmitted to the base module 130. The base module 130 may receive an acknowledgement that the pre-operative plan was determined in the process 400.

Moreover, the computer system can transmit the pre-operative plan to one or more components of the surgical robot 100, including but not limited to the processor 108 and/or the user interface 120. As described herein, the processor 108 can configure components of the surgical arm according to the pre-operative plan and/or determine initial laser settings based on the pre-operative plan (e.g., refer to FIG. 5). The practitioner, such as Dr. Van, can review the pre-operative plan at the user interface 120. Sometimes, the practitioner can suggest one or more additional or different adjustments to the pre-operative plan at the user interface 120. Such adjustments can be transmitted to the computer system and implemented before the surgical procedure begins.

Figure 5:
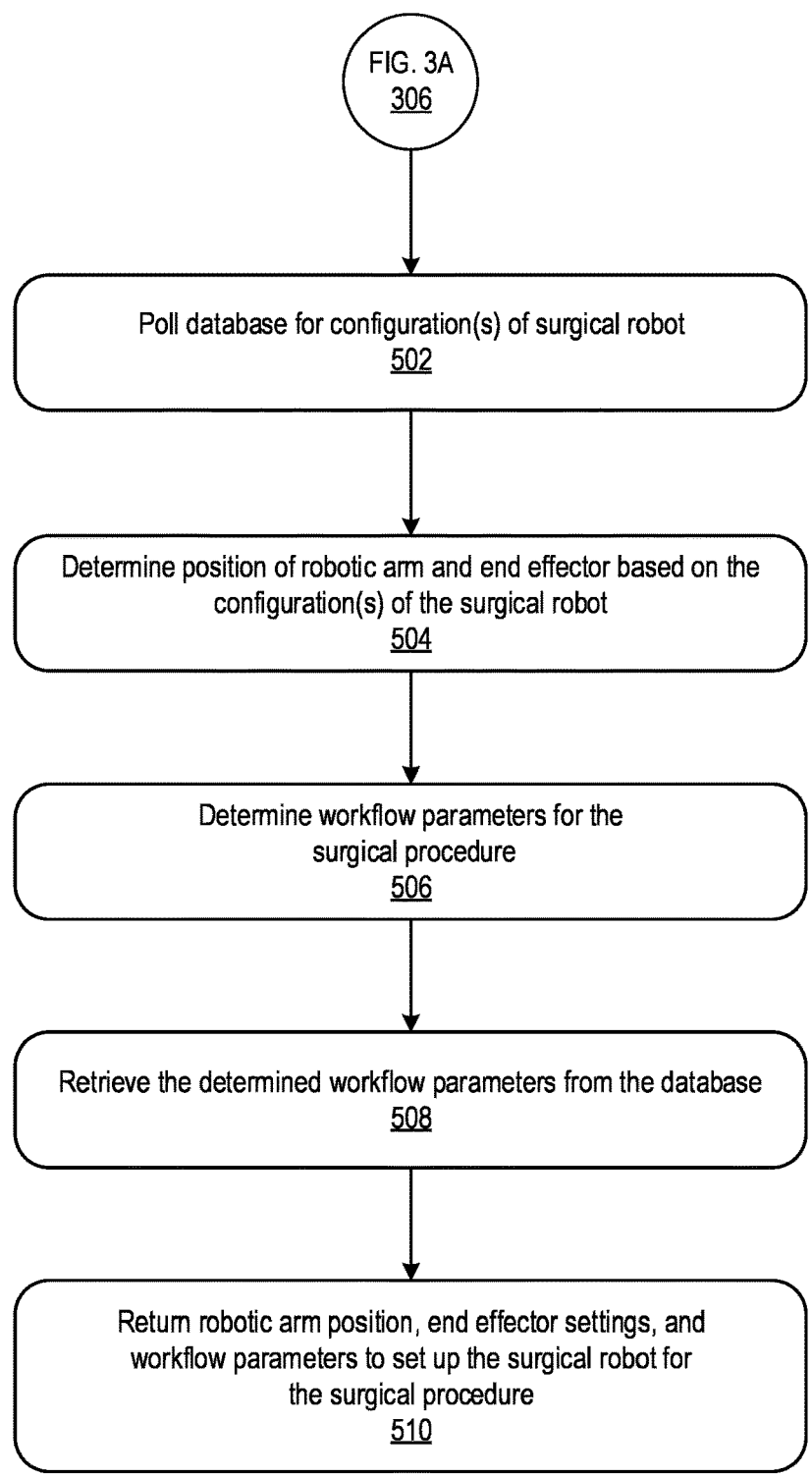
FIG. 5 is a flowchart of a process for setting up a laser for a robotic laser surgery.

FIG. 5 is a flowchart of a process 500 for setting up a laser for a robotic laser surgery. The process 500 can also be used to perform any other type of procedure that can use the surgical robot 100 described herein. The process 500 can be performed by the computer system 160 described in reference to FIGS. 1A-B. In some implementations, one or more blocks of the process 300 can be performed by one or more of the modules 130, 132, 134, 136, 138, and 140 described in reference to FIG. 1B. The process 500 can also be performed by one or more other computing systems, devices, computers, networks, cloud-based systems, and/or cloud-based services. For illustrative purposes, the process 500 is described from the perspective of a computer system.

Referring to the process 500 in FIG. 5, the computer system can poll a database for configuration(s) of the surgical robot 100 (block 502). For example, the laser setup module 134 may receive a prompt from the base module 130 (block 306 in FIG. 3A) to set up the laser before the surgical procedure begins. The laser setup module 134 may poll the operation database 118 (or the database 158) for configuration settings/information that may be required of the surgical robot 100 to perform the surgical procedure. In some implementations, the laser setup module 134 may poll the operation database 118 for different types of tissues to be touched during the surgical procedure. For example patient Alex, the laser setup module 134 can poll the operation database 118 for types of tissue that would be removed for Alex's upcoming surgical procedure. The database 118 can return cancerous cells in Alex's lungs as well as a list of healthy tissues surrounding the cancerous cells. The database 118 may also return a list of areas (e.g., tissues) where laser intensity can be adjusted based on the pre-operative plan. Thus, the laser setup module 134 can retrieve different configurations for the surgical robot 100 before proceeding with the surgical procedure. The different configurations can also include maximum intensity, beam size, and movement speed for components of the surgical robot 100, such as the laser 106. For example, the database 118 can return maximum intensity settings for the particular laser 106 to be used during the surgical procedure.

The computer system can then determine a position of the robotic arm of the surgical robot 100 and an end effector of the surgical robot 100 based on the configuration(s) of the surgical robot (block 504). For example, the laser setup module 134 may be configured to determine the position of the robotic arm 102 and the end effector 104. In some implementations, the laser setup module 134 may determine an initial position of the end effector 104 and the robotic arm 102 using image data that can be collected of a surgical area from the imaging devices 112. For example, if the robotic arm 102 and the end effector 104 with the tunable laser 106 are positioned towards example patient Alex at 35 degrees of inclination, the imaging devices 112 may detect the position and transmit it to the user interface 120 and/or the laser setup module 134 at the computer system 160. The laser setup module 134 can determine, based on the image data, that the position of the robotic arm 102, the end effector 104, and the laser 106 should be adjusted to an inclination of 30 degrees. This determination can be made based on expected degrees of inclination for the surgical robot 100 in similar/same surgical procedures (which can be received in block 502).

The computer system can also determine workflow parameters for the surgical procedure in block 506. The laser setup module 134 can determine which workflow parameters to retrieve for the particular surgical procedure based on the pre-operative plan. For example, the laser setup module 134 can determine preferred workflow parameters for removing cancerous cells from the lungs based on information in the pre-operative plan for example patient Alex.

The computer system can then retrieve the determined workflow parameters from the database in block 508. For example, the computer system can poll the database for workflow parameters that are associated with the pre-operative plan. The laser setup module 134 may retrieve preferred workflow parameters from the operation database 118. As an illustrative example, the preferred workflow parameters related to the removal of cancerous cells from the lungs of example patient Alex may be that the laser intensity be kept at 15 W/cm$^2$ when ablating center of cancerous cells and the laser intensity can then be decreased to 10 W/cm$^2$ when reaching near the non-ablated areas of the lungs, and then automatically stopped to 0 W/cm$^2$ when reaching a boundary of the cancerous cells. The preferred workflow parameters can also include position information of the robotic arm 102 and the end effector 104 being inclined at 30 degrees northwards. The workflow parameters can thus be used to dynamically and automatically adjust the surgical robot 100 during the surgical procedure.

The computer system can then return the robotic arm position, end effector settings, and/or workflow parameters to set up the surgical robot 100 for the surgical procedure (block 510). In some implementations, the computer system can automatically adjust the robotic arm 102 to the desired position and otherwise adjust the end effector to initial settings before the surgical procedure begins. In some implementations, the robotic arm position, end effector settings, and/or workflow parameters can be transmitted/provided to another component of the computer system 160 or the processors 108 of the surgical robot 100, which can be configure to adjust initial settings of the surgical robot 100 before the surgical procedure begins. Moreover, in block 510, the laser setup module 134 may send a laser ready status to the base module. The laser ready status can indicate that the surgical robot 100 has been set to initial settings and thus is ready to begin performing the surgical procedure.

Figure 6:
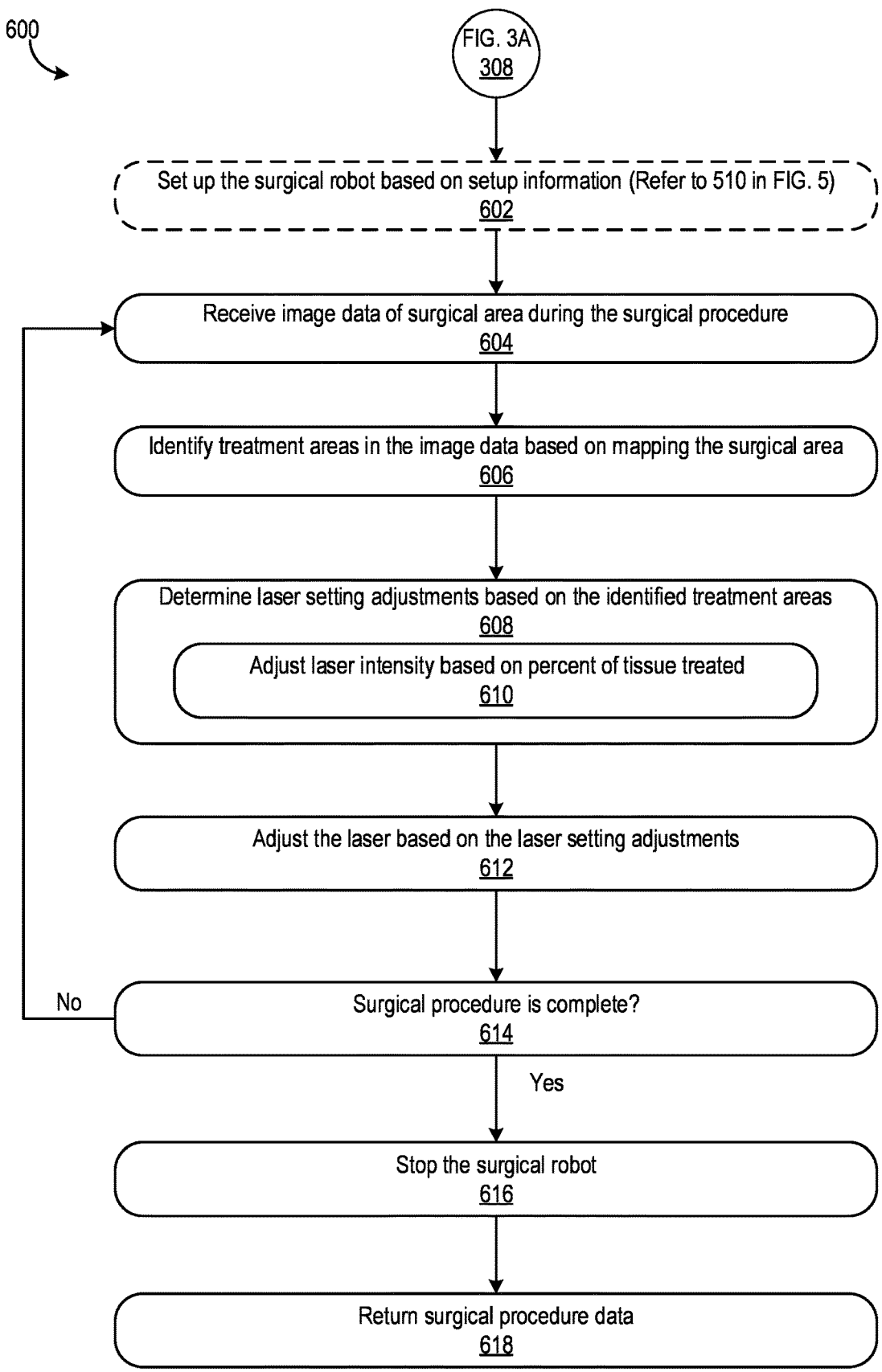
FIG. 6 is a flowchart of a process for performing a robotic laser surgery.

FIG. 6 is a flowchart of a process 600 for performing a robotic laser surgery. The process 600 can also be used to perform any other type of procedure that can use the surgical robot 100 described herein. The process 600 can be performed by the computer system 160 described in reference to FIGS. 1A-B. In some implementations, one or more blocks of the process 600 can be performed by one or more of the modules 130, 132, 134, 136, 138, and 140 described in reference to FIG. 1B. The process 600 can also be performed by one or more other computing systems, devices, computers, networks, cloud-based systems, and/or cloud-based services. For illustrative purposes, the process 600 is described from the perspective of a computer system.

Referring to the process 600 in FIG. 6, the computer system can optionally set up the surgical robot 100 based on setup information (block 602). The setup information can be returned in block 510 in FIG. 5. Initial settings (e.g., position, orientation, laser intensity, etc.) of the laser 106, the end effector 104, and/or the robotic arm 102 can be made in block 602. In some implementations, as described in reference to the process 500 in FIG. 5, the components of the surgical robot 100 may already be set up in block 510. Thus, block 602 may not be performed in the process 600.

Once the surgical robot 100 is set up, the surgical procedure can begin. Therefore, the computer system can receive image data of a surgical area during the surgical procedure in block 604. The image data can be continuously received so long as the surgical procedure is being performed. In some implementations, image data can also be received before the surgical procedure in order to determine one or more of the setup information (e.g., refer to the process 500 in FIG. 5). Sometimes, the image data may not be received until the operation module 138 receives a prompt from the base module 130 (e.g., refer to block 308 in FIG. 3A). The prompt may indicate that the surgical robot 100 is set up and the surgical procedure can begin. The prompt can also indicate that the imaging devices 112 should be activated or otherwise instructed to begin capturing image data of the surgical area. Accordingly, the operation module 138 may be configured to instruct the imaging devices 112 to image the surgical area while performing the surgical procedure.

As described herein, the imaging devices 112 can include, but are not limited to, optical sensors that can detect the surgical area on the patient's body where the surgical procedure is to be performed and/or is currently being performed. For example, for example patient Alex, the diagnosis can be lung cancer. Therefore, the operation module 138 can direct the optical sensors of the imaging devices 112 towards Alex's chest to image the chest. The operation module 138 can then use this image data to determine where a cut is to be made and where cancerous cells need to be ablated (e.g., refer to blocks 606-608).

Accordingly, the computer system can identify treatment areas in the image data based on mapping the surgical area in block 606. As an illustrative example, the computer system can implement techniques, such as an algorithm, for identifying pixels in the image data to detect edges. The detected edges can then be identified as a region for which to apply the laser. A surgeon (or a robotic arm, as described herein) can direct the laser (e.g., using an interface, such as a GUI presented at the user device 120 described above) by identifying anatomical structure that were defined by boundaries in image data before the surgical procedure. The image data can be generated using preoperative CT scans, fluoroscopy, and other medical imaging techniques. A real-time camera can have a same image inter-operatively and therefore can be used to guide the laser based on predefined boundaries.

As another illustrative example, a fluoroscope can be used to identify fluoroscopic waveform of the surgical area. Using AI-based rules, the fluoroscopic waveform in fluoroscopic data can be used by the computer system to guide the laser. Image data from inter-operative cameras may also be used by the computer system to draw a lesion on the image data and to train a machine learning model used for identifying surgical boundaries. The machine learning model can be trained to suggest boundaries to the surgeon, which the surgeon can accept, reject, or correct during surgical procedures. The surgeon's response to the machine learning model's output can further be used for continuous training of the machine learning model.

As described above, the operation module 138 may map the surgical area to identify the ablation areas. Sometimes, the operation module 138 may also employ the sensors 110 and the imaging devices 112 to simulate a map for the surgical area. For example patient Alex, the sensors 110 can detect temperature values of Alex's imaged chest. When combined/correlated with the image data of Alex's chest, the computer system can generate a map of Alex's chest that differentiates areas with the cancerous cells from healthy or non-cancerous areas, such as Alex's lungs. The computer system can overlay the image data with the temperature data. Different ranges of temperature values can be attributed to different types of cells (e.g., cancerous cells versus non-cancerous cells/organs). Therefore, the computer system can identify the different temperature values that were detected, correlate those temperature values with known temperature ranges for different types of cells, and then identify where in the surgical area those types of cells are located. The computer system can use the identified locations as reference points for determining adjustments to the surgical robot 100.

The computer system can determine laser setting adjustments based on the identified treatment areas in block 608. For example, the computer system can determine adjustments to the laser intensity based on a percent of tissue being treated during the surgical procedure (block 610). The operation module 138 may set initial intensity for the surgical robot 100. In one embodiment, the operation module 138 may set the intensity of the tunable laser 106 when it is directed towards the treatment area. For example patient Alex, the initial intensity of the laser 106 can be set at 15 $W/cm^2$, as the laser 106 is initially directed towards a center of the cancerous cells of Alex's lungs. Successively, the operation module 138 may be configured to ablate tissues from the treatment area, then stop and reassess, as described in blocks 604-614.

With regards to block 610, the operation module 138 may be configured to adjust the intensity of the surgical robot 100 with respect to a percentage of tissue being ablated. For example patient Alex, when the laser 106 ablates 30% of the cancerous cells from Alex's lungs with laser intensity at 15 $W/cm^2$, the operation module 138 may determine to decrease the intensity of the laser 106 to 10 $W/cm^2$ as the end effector 104 moves towards a boundary of the cancerous cells.

The computer system can then adjust the laser based on the laser setting adjustments in block 612. For example, the operation module 138 may be configured to dynamically and successively position the surgical robot 100 towards the identified treatment areas (e.g., ablation areas). In some implementations, the operation module 138 may receive an input signal from the user interface 120 to position the surgical robot 100 towards an identified treatment area. For example, the practitioner can manually orient the robotic arm 102, the end effector 104, and/or the laser 106 using one or more robot controls that are provided via the user interface 120. In some implementations, the operation module 138 may automatically orient the robotic arm 102, the end effector 104, and/or the laser 106 towards the identified treatment area. For example, the operation module 138 may automatically orient the tunable laser 106 towards Alex's lungs with 30 degree inclination towards a north side of the treatment area.

The surgical procedure can continue to be performed. The computer system can determine whether the surgical procedure is complete in block 614. This determination can be made based on analysis of the image data that is continuously received of the surgical area (block 604). So long as the surgical procedure is not complete, the computer system can repeat blocks 604-612. Once the computer system determines the surgical procedure is complete, the computer system can proceed to block 616, described below.

In the example surgical procedure for Alex, the tunable laser 106, with initial intensity set at 15 $W/cm^2$, can ablate some cells from the center of the cancerous cells. During the procedure, the laser 106 can then be stopped momentarily so that the imaging devices 112 can detect and image progress of the ablation and transit the image data to the computer system 160 and/or the user interface 120. Then, the operation module 138 can evaluate a quantity of cancerous cells being ablated to determine how the laser 106 can be adjusted to proceed with further ablation. For example, with initial intensity set at 15 $W/cm^2$, the laser may only ablate 20% of cancerous cells towards the north side of the treatment area once it reaches near a boundary of the treatment area. The operation module 138 can determine one or more adjustments to laser intensity to complete the surgical procedure.

The laser intensity may be adjusted continuously while ablating tissues from the ablation area or while the laser is continuously firing towards the treatment area. The operation module 138 may also adjust the laser intensity after the tunable laser stops firing towards the treatment area, and then may resume firing towards the ablation area once the laser intensity is adjusted.

In the example of Alex's surgery, Dr Van may manually control the robotic arm 102 to turn on the end effector 104 to initiate firing of the laser 106 towards the cancerous cells of Alex's lungs after the laser 106 is automatically adjusted (by the operation module 138) to 10 $W/cm^2$ from 15 $W/cm^2$.

This adjustment can be determined and made once the computer system determines that the laser 106 has already ablated 30% of the cancerous cells from Alex's lungs. During adjustment of the laser intensity, Dr. Van may first receive progress updates about adjustments and ablation from the imaging devices 112 and/or the computer system 160.

If the computer system determines that the surgical procedure is complete in block 614, the computer system can stop the surgical robot 100 in block 616. For example, the operation module 138 may be configured to stop the surgical robot 100 when the surgical procedure is completed. The operation module 138 may automatically stop the end effector 104 when the laser 106 hits a boundary of the treatment area, as determined based on analysis of the image data received continuously in block 604. The operation module 138 may also automatically stop the end effector 104 when the surgical procedure is completed, which can be determined based on a determination, by the computer system, that 100% or almost 100% of the surgical area has been treated.

For example, when the computer system determines that 99% of the cancerous cells of Alex's lungs are ablated based on analysis of the image data from the imaging devices 112, the computer system may initiate a signal indicating that the surgical process has reached near 100%. The operation module 138 may then automatically adjust the laser intensity to 0 W/cm$^2$ and stop the laser 106 from firing towards the ablation or non-ablation area of Alex's lungs. The imaging devices 112 can continue to capture image data of the ablation area, and this image data can be analyzed by the computer system do determine whether the cancerous cells have been completely removed or not.

In some implementations, after the surgical robot 100 is stopped in block 616, the computer system can instruct the imaging devices 112 to perform a full scan over the treatment area to determine whether any cancerous cells or other tissues are still present and if any healthy or non-cancerous cell have been ablated during the surgical procedure. This can be performed as part of determining whether the surgical procedure is complete in block 614.

The computer system can then return surgical procedure data in block 618. For example, the operation module 138 may be configured to send feedback to the user interface 120 about the surgical procedure. The operation module 318 can send a variety of data, monitored data, and/or analytics performed by the computer system to the user interface 120. For example, the operation module 138 may send, to the user interface 120, adjustments to the laser intensity of the tunable laser 106 that were made throughout the surgical procedure, a percentage of cancerous cells or other tissues removed, a percentage of non-cancerous cells removed (if any), and/or orientation and/or position information of the robotic arm 102 and the end effector 104 throughout the surgical procedure. For example patient Alex, the operation module 138 can include information (i) about adjusting the laser intensity of the tunable laser 106 from 15-0 W/cm$^2$, (ii) 99.8% of cancerous cells being removed, (iii) 0.02% of non-cancerous cells being removed, and (iv) the robotic arm 102 being held at 30-degree inclination northwards while throughout the surgical procedure. The surgical procedure data can also be stored in a database, such as the database 158 and/or the database 118, in block 618.

Figure 7:
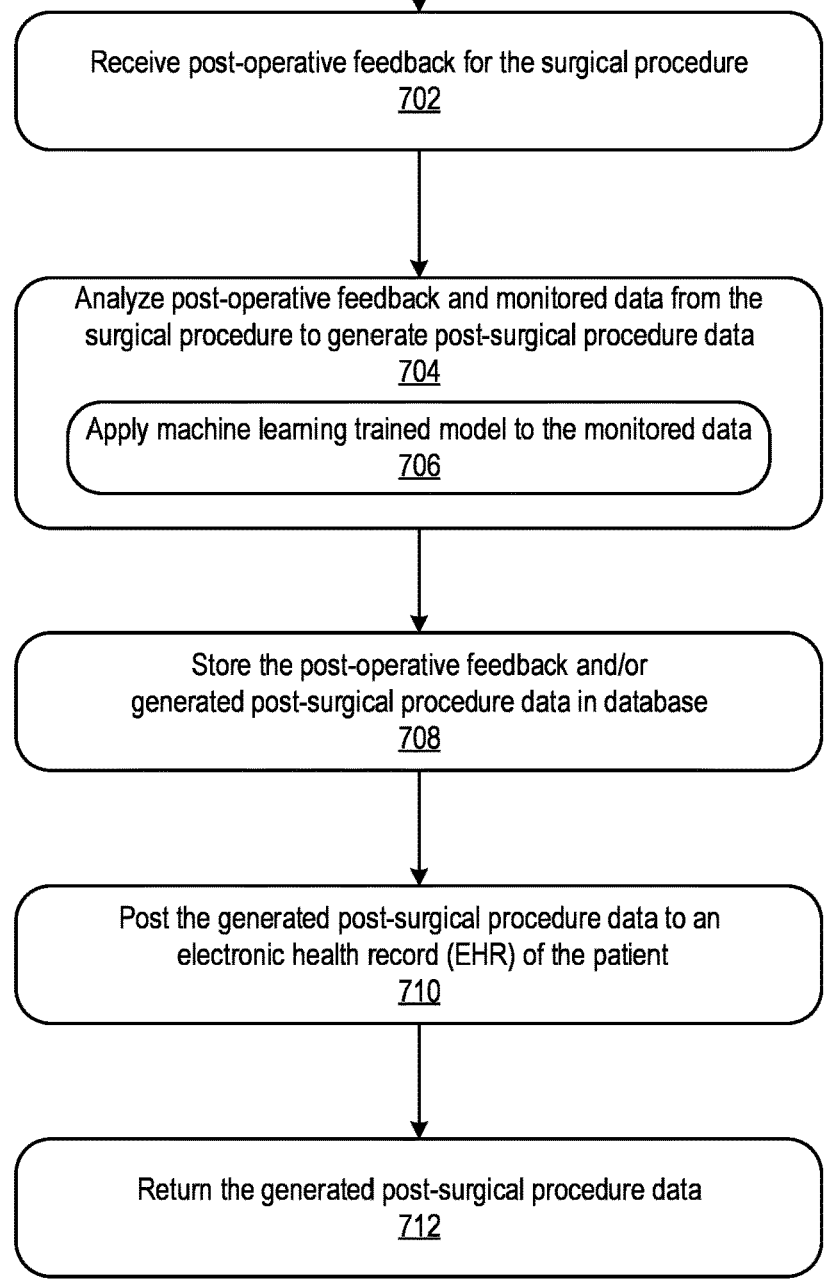
FIG. 7 is a flowchart of a process for completing and closing a robotic laser surgery.

FIG. 7 is a flowchart of a process 700 for completing and closing a robotic laser surgery. The process 700 can also be used to perform any other type of procedure that can use the surgical robot 100 described herein. The process 700 can be performed by the computer system 160 described in reference to FIGS. 1A-B. In some implementations, one or more blocks of the process 700 can be performed by one or more of the modules 130, 132, 134, 136, 138, and 140 described in reference to FIG. 1B. The process 700 can also be performed by one or more other computing systems, devices, computers, networks, cloud-based systems, and/or cloud-based services. For illustrative purposes, the process 700 is described from the perspective of a computer system.

Referring to the process 700 in FIG. 7, the computer system can receive post-operative feedback for the surgical procedure in block 702. For example, the operation close module 140 may receive a prompt from the base module 130 (e.g., refer to block 316 in FIG. 3B). The operation close module 140 may collect post-operative feedback from the surgical robot 100, such as from the user interface 120. In some implementations, the surgical robot 100, via the user interface 120, may provide feedback after the surgical procedure is completed. For example, Dr. Van can provide a detailed chart related to removal of cancerous cells from Alex's lungs. The operation close module 140 can also collect information such as the pre-operative plan from the operation database 118 and parameters that were adjusted during treatment of the patient's tissue(s). In the example of Alex's surgery, Dr. Van can provide input indicating that the laser intensity of the tunable laser 106 was adjusted from 15-0 W/cm$^2$ and that Alex was stable during the surgical procedure, subject to a decrease in blood pressure from 80 to 65 bpm, which was controlled during the surgical procedure. In some implementations, the computer system can also receive any of the monitored data from the imaging devices 112 and/or the sensors 110 in block 702.

In block 704, the computer system can analyze the post-operative feedback and monitored data from the surgical procedure to generate post-surgical procedure data. For example, the computer system can apply one or more machine learning trained models and/or machine learning algorithms/techniques to the post-operative feedback and/or the monitored data (block 706).

The operation close module 140 may analyze the monitored data, such as optical information in image data that was continuously received from the imaging devices 112 during the surgical procedure. Machine learning techniques can be used by the computer system to assess the surgical procedure and compare the surgical procedure with surgical procedures that had been previously conducted. For example, the operation close module 140 can determine that 10% of healthy tissues have been ablated in a particular surgical procedure compared to previous similar/same surgical procedures. The computer system can also determine how much time the practitioner was present or absent from the surgical procedure and how the practitioner's presence or absence impacted the surgical procedure. For example, during Alex's 95 minute surgical procedure, Dr. Van might have been 4 minutes off the mark when the surgical procedure proceeded to 47$^{th}$ minute of the surgical procedure.

In blocks 704 and 706, the operation close module 140 may also evaluate ratings of the practitioners against historic metrics or other data accessible from the database 118 with respect to previous surgical procedures. The operation close module 140 can then determine an overall rating of the practitioner. In the example of Alex's surgery, the operation close module 140 may assign Dr. Van a rating of 4.5 out of 5 (e.g., 4.5 out of 5 stars) based on the removal of 99.8% of cancerous cells, removal of 0.02% of healthy cells, maintenance of stable conditions of Alex during the procedure, and only being off the mark for 4 minutes during the surgical procedure.

In block 708, the computer system can store the post-operative feedback and/or generated post-surgical procedure data in the database (e.g., the database 158 and/or 118). The computer system can also post the generated post-surgical procedure data to EHR of the patient (block 710). For example patient Alex, the operation close module 140 may post all the surgical procedure data in the operation database 118 and/or the EHR, including but not limited to the laser intensity being adjusted from 15-0 W/cm$^2$, orientation of the robotic arm 102 at various different times during the surgical procedure (e.g., orientations of 10 cm, 12 cm, and 9 cm), 99.8% of cancerous cells being removed, 0.02% of healthy cells being removed, a duration of the surgical procedure (e.g., 95 minutes), a condition of Alex during the surgical procedure (e.g., bpm reduction from 85 to 65).

Sometimes, the operation close module 140 may post less than all of the surgical procedure data to the EHR or otherwise in a data record in the database. For example, the operation close module 140 may not post data about Alex's condition during the surgical procedure. The operation close module 140 may also eliminate or otherwise discard some irrelevant data, such as information related to the Health Insurance Portability and Accountability Act (HIPAA). Therefore, patient privacy can be maintained.

The computer system can also return the generated post-surgical procedure data in block 712. For example, this data can be transmitted to the user interface 120 to be presented to and reviewed by the practitioner. In some implementations, the operation close module 140 may send this data to the base module 130 of the computer system 160. Successively, the base module 130 may receive the generated post-surgical procedure data from the operation close module 140. The base module 130 can then transmit the continuously received data to the user interface 120 and/or store this data in the database.

In some implementations, the surgical procedure described throughout this disclosure may be fully autonomous by the surgical robot 100, without interference of the robotic arm 102 or manual adjustments by the practitioner at the user interface 120. In some implementations, the surgical procedure may be fully and/or partly manual by the practitioner using the robotic arm 102 and/or controls at the user interface 120. In some implementations, the surgical procedure may be a hybrid surgical procedure in which one or more components of the surgical robot can be controlled by the robotic arm 102, one or more components can be controlled by the surgical robot 100, and/or one or more components can be controlled by the practitioner from the user interface 120. The surgical robot 100 may also operate in a semiautonomous mode in which the practitioner can act as a check on the surgical robot 100, the surgical robot 100 can propose an action or actions to take (e.g., adjustments to components of the surgical robot 100, a way in which the surgical procedure is to be performed, etc.), and the action can be approved by the practitioner at the user interface 120 before the surgical robot 100 executes the action. In some implementations, during the hybrid surgical procedure, the surgical robot 100 may hand over some part/steps in a workflow of the surgical procedure to the robotic arm 102, such as when sensitive areas of the patient's body may require the practitioner to manually control surgical tools that are being used. The robotic arm 102 may then pass the control back to the surgical robot 100 in an autonomous mode or after the part/steps in the workflow involving the sensitive areas are completed.

Figure 8:
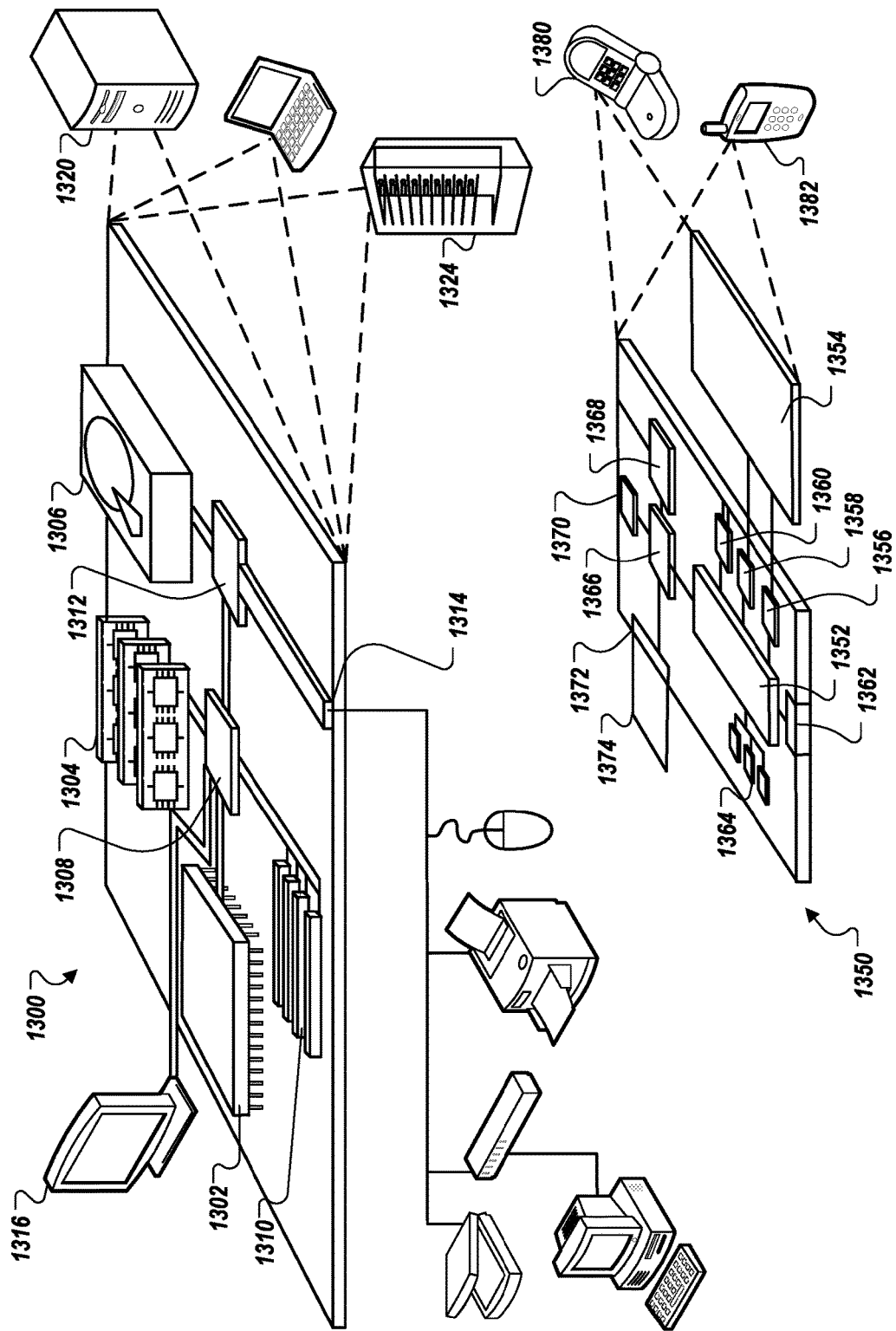
FIG. 8 is a schematic diagram that shows an example of a computing device and a mobile computing device.

FIG. 8 shows an example of a computing device 800 and an example of a mobile computing device that can be used to implement the techniques described here. The computing device 800 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 800 includes a processor 802, a memory 804, a storage device 806, a high-speed interface 808 connecting to the memory 804 and multiple high-speed expansion ports 810, and a low-speed interface 812 connecting to a low-speed expansion port 814 and the storage device 806. Each of the processor 802, the memory 804, the storage device 806, the high-speed interface 808, the high-speed expansion ports 810, and the low-speed interface 812, are interconnected using various busses, and can be mounted on a common motherboard or in other manners as appropriate. The processor 802 can process instructions for execution within the computing device 800, including instructions stored in the memory 804 or on the storage device 806 to display graphical information for a GUI on an external input/output device, such as a display 816 coupled to the high-speed interface 808. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 804 stores information within the computing device 800. In some implementations, the memory 804 is a volatile memory unit or units. In some implementations, the memory 804 is a non-volatile memory unit or units. The memory 804 can also be another form of computer-readable medium, such as a magnetic or optical disk.

The storage device 806 is capable of providing mass storage for the computing device 800. In some implementations, the storage device 806 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 804, the storage device 806, or memory on the processor 802.

The high-speed interface 808 manages bandwidth-intensive operations for the computing device 800, while the low-speed interface 812 manages lower bandwidth-intensive operations. Such allocation of functions is exemplary only. In some implementations, the high-speed interface 808 is coupled to the memory 804, the display 816 (e.g., through a graphics processor or accelerator), and to the high-speed expansion ports 810, which can accept various expansion cards (not shown). In the implementation, the low-speed interface 812 is coupled to the storage device 806 and the low-speed expansion port 814. The low-speed expansion port 814, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 800 can be implemented in a number of different forms, as shown in the figure. For example, it can be implemented as a standard server 820, or multiple times in a group of such servers. In addition, it can be implemented in a personal computer such as a laptop computer 822. It can also be implemented as part of a rack server system 824. Alternatively, components from the computing device 800 can be combined with other components in a mobile device (not shown), such as a mobile computing device 850. Each of such devices can contain one or more of the computing device 800 and the mobile computing device 850, and an entire system can be made up of multiple computing devices communicating with each other.

The mobile computing device 850 includes a processor 852, a memory 864, an input/output device such as a display 854, a communication interface 866, and a transceiver 868, among other components. The mobile computing device 850 can also be provided with a storage device, such as a micro-drive or other device, to provide additional storage. Each of the processor 852, the memory 864, the display 854, the communication interface 866, and the transceiver 868, are interconnected using various buses, and several of the components can be mounted on a common motherboard or in other manners as appropriate.

The processor 852 can execute instructions within the mobile computing device 850, including instructions stored in the memory 864. The processor 852 can be implemented as a chipset of chips that include separate and multiple analog and digital processors. The processor 852 can provide, for example, for coordination of the other components of the mobile computing device 850, such as control of user interfaces, applications run by the mobile computing device 850, and wireless communication by the mobile computing device 850.

The processor 852 can communicate with a user through a control interface 858 and a display interface 856 coupled to the display 854. The display 854 can be, for example, a TFT (Thin-Film-Transistor Liquid Crystal Display) display or an OLED (Organic Light Emitting Diode) display, or other appropriate display technology. The display interface 856 can comprise appropriate circuitry for driving the display 854 to present graphical and other information to a user. The control interface 858 can receive commands from a user and convert them for submission to the processor 852. In addition, an external interface 862 can provide communication with the processor 852, so as to enable near area communication of the mobile computing device 850 with other devices. The external interface 862 can provide, for example, for wired communication in some implementations, or for wireless communication in other implementations, and multiple interfaces can also be used.

The memory 864 stores information within the mobile computing device 850. The memory 864 can be implemented as one or more of a computer-readable medium or media, a volatile memory unit or units, or a non-volatile memory unit or units. An expansion memory 874 can also be provided and connected to the mobile computing device 850 through an expansion interface 872, which can include, for example, a SIMM (Single In Line Memory Module) card interface. The expansion memory 874 can provide extra storage space for the mobile computing device 850, or can also store applications or other information for the mobile computing device 850. Specifically, the expansion memory 874 can include instructions to carry out or supplement the processes described above, and can include secure information also. Thus, for example, the expansion memory 874 can be provide as a security module for the mobile computing device 850, and can be programmed with instructions that permit secure use of the mobile computing device 850. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 864, the expansion memory 874, or memory on the processor 852. In some implementations, the computer program product can be received in a propagated signal, for example, over the transceiver 868 or the external interface 862.

The mobile computing device 850 can communicate wirelessly through the communication interface 866, which can include digital signal processing circuitry where necessary. The communication interface 866 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 868 using a radio-frequency. In addition, short-range communication can occur, such as using a Bluetooth, WiFi, or other such transceiver (not shown). In addition, a GPS (Global Positioning System) receiver module 870 can provide additional navigation- and location-related wireless data to the mobile computing device 850, which can be used as appropriate by applications running on the mobile computing device 850.

The mobile computing device 850 can also communicate audibly using an audio codec 860, which can receive spoken information from a user and convert it to usable digital information. The audio codec 860 can likewise generate audible sound for a user, such as through a speaker, e.g., in a handset of the mobile computing device 850. Such sound can include sound from voice telephone calls, can include recorded sound (e.g., voice messages, music files, etc.) and can also include sound generated by applications operating on the mobile computing device 850.

The mobile computing device 850 can be implemented in a number of different forms, as shown in the figure. For example, it can be implemented as a cellular telephone 880. It can also be implemented as part of a smart-phone 882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as disclosed above.

What is claimed is:

1. A system for performing autonomous and semi-autonomous surgical procedures with a surgical laser, the system comprising:
 a surgical robot configured to perform a surgical procedure on a patient, the surgical robot including:
  a robotic arm;
  a laser that is attached to the robotic arm and configured to emit a surgical laser beam based on one or more laser settings;
  at least one imaging device that is configured to continuously capture image data of a surgical area of the patient; and
  at least one sensor that is configured to continuously capture sensor data of at least one of the surgical robot and the patient; and
 a surgical computing system in communication with the surgical robot, wherein the surgical computing system is configured to, before the surgical procedure:
  retrieve, from a data store, at least one of historic patient data and historic surgical procedure data;
  determine, based on the retrieved data, a pre-operative plan, wherein the pre-operative plan includes initial laser settings for the laser; and
  transmit, to the surgical robot, the pre-operative plan, wherein the laser adjusts the one or more laser settings to the initial laser settings in response the surgical robot receiving the pre-operative plan; and
 wherein the surgical computing system is configured to, during the surgical procedure:
  continuously receive, from the at least one imaging device and the at least one sensor, the image data and the sensor data;
  determine, based on the received data, at least one adjustment to the initial laser settings; and
  transmit, to the surgical robot, the at least one adjustment to the initial laser settings, wherein the laser automatically adjusts the one or more laser settings based on the at least one adjustment during the surgical procedure,
 wherein the surgical computing system comprises:
  a base module configured to receive an indication from a computing system to prepare the pre-operative plan for the surgical procedure, wherein the computing system is different than the surgical computing system;

a pre-operative module configured to receive a request from the base module to generate the pre-operative plan;

a laser setup module configured to (i) receive a request from the base module to generate instructions for causing the laser to automatically adjust the one or more laser settings to the initial laser settings based on the pre-operative plan, and (ii) receive at least one additional request from the base module to generate instructions that cause the laser to automatically adjust the one or more laser settings during the surgical procedure and based on at least one of the image data and the sensor data;

an operation module configured to receive a request from the base module to cause the surgical robot to perform the surgical procedure based at least in part on the pre-operative plan and at least one of the image data and the sensor data; and an operation close module configured to determine that the surgical procedure is complete and to generate post-surgical procedure data based at least in part on the pre-operative plan, one or more adjustments that were made to the one or more laser settings during the surgical procedure, and at least one of the image data and the sensor data.

2. The system of claim 1, wherein the surgical computing system is further configured to transmit to a user device, for presentation in a graphical user interface (GUI) display, at least one of the pre-operative plan, the initial laser settings, the image data, the sensor data, and the at least one adjustment to the one or more laser settings.

3. The system of claim 1, wherein the surgical computing system is configured to determine, during the surgical procedure, at least one adjustment to the initial laser settings based on:

identifying a treatment area in the image data based on mapping the surgical area that is captured in the image data;

determining a quantity of treated tissue in the identified treatment area; and determining, based on the quantity of treated tissue, the at least one adjustment to the initial laser settings.

4. The system of claim 3, wherein the surgical computing system is configured to determine the at least one adjustment to the initial laser settings based on a determination that the laser is within a threshold distance from a boundary of the identified treatment area, wherein the at least one adjustment includes rotating the laser such that the laser is oriented away from the boundary of the identified treatment area.

5. The system of claim 1, wherein the laser settings include at least one of a laser beam intensity, a size of a beam emitted by the laser, an amount of energy expelled by the laser, a position of the laser relative to the surgical area, and an orientation of the laser relative to the surgical area.

6. The system of claim 1, wherein the surgical computing system is further configured to determine that the surgical procedure is complete based at least in part on the image data and the sensor data.

7. The system of claim 6, wherein the surgical computing system is configured to determine that the surgical procedure is complete based on:

identifying a treatment area in the image data based on mapping the surgical area that is captured in the image data;

determining a quantity of treated tissue in the identified treatment area; and determining that the quantity of treated tissue exceeds a threshold value.

8. The system of claim 6, wherein the surgical computing system is further configured to generate post-surgical procedure data based on applying a machine learning model to at least one of the image data and the sensor data, wherein the machine learning model was trained to generate a comparison of monitored surgical procedure data to historic surgical procedure data using a training data set, wherein the monitored surgical procedure data and the historic surgical procedure data are a same type of procedure as the surgical procedure.

9. The system of claim 8, wherein the surgical computing system is further configured to generate the post-surgical procedure data based on post-operative feedback received from a user device of a practitioner assigned to the surgical procedure.

10. The system of claim 8, wherein the surgical computing system is configured to post the post-surgical procedure data to an electronic health record (EHR) of the patient.

11. The system of claim 1, wherein the one or more laser settings include a laser intensity.

12. The system of claim 1, wherein the one or more laser settings include a size of a beam emitted by the laser.

13. The system of claim 1, wherein the one or more laser settings include an amount of energy expelled by the laser.

14. The system of claim 1, wherein the one or more laser settings include a position of the laser relative to at least one of the surgical area and a boundary of the surgical area.

15. The system of claim 1, wherein the one or more laser settings include an orientation of the laser relative to at least one of the surgical area and a boundary of the surgical area.

16. A surgical laser of a surgical robot that is used for performing autonomous and semi-autonomous surgical procedures, the surgical laser being configured to:

receive, from a surgical computing system in communication with the surgical robot and before a surgical procedure, initial laser settings for the laser, wherein the initial laser settings were determined, by the surgical computing system, as part of a pre-operative plan for the surgical procedure based on at least one of historic patient data and historic surgical procedure data;

automatically adjust, before the surgical procedure, one or more laser settings to the initial laser settings;

perform the surgical procedure based on the adjusted one or more laser settings;

receive, from the surgical computing system and during the surgical procedure, at least one adjustment to the initial laser settings; and automatically adjust, during the procedure, the one or more laser settings based on the at least one adjustment received during the surgical procedure, wherein the surgical laser is attached to a robotic arm of a surgical robot and configured to emit a surgical laser beam during the surgical procedure and based on the one or more laser settings, wherein the surgical computing system comprises:

a base module configured to receive an indication from a computing system to prepare the pre-operative plan for the surgical procedure, wherein the computing system is different than the surgical computing system;

a pre-operative module configured to receive a request from the base module to generate the pre-operative plan;

a laser setup module configured to (i) receive a request from the base module to generate instructions for causing the laser to automatically adjust the one or more laser settings to the initial laser settings based on the pre-operative plan, and (ii) receive at least one additional request from the base module to generate instructions that cause the laser to automatically adjust the one or more laser settings during the surgical procedure and based on at least one of image data and sensor data;

an operation module configured to receive a request from the base module to cause the surgical robot to perform the surgical procedure based at least in part on the pre-operative plan and at least one of the image data and the sensor data; and an operation close module configured to determine that the surgical procedure is complete and to generate post-surgical procedure data based at least in part on the pre-operative plan, one or more adjustments that were made to the one or more laser settings during the surgical procedure, and at least one of the image data and the sensor data.

17. The surgical laser of claim 16, wherein the surgical laser receives the at least one adjustment, from the surgical computing system and during the surgical procedure, based on a determination, by the surgical computing system, that the surgical laser is within a threshold distance from a boundary of a surgical area of a patient during the surgical procedure, wherein the at least one adjustment includes rotating the surgical laser a predetermined amount of degrees such that the surgical laser is oriented away from the boundary of the surgical area.

18. The surgical laser of claim 16, wherein the surgical laser is configured to:
temporarily stop performing the surgical procedure as the surgical laser automatically adjusts the one or more laser settings; and
resume performing the surgical procedure once the surgical laser completes automatically adjusting the one or more laser settings.

19. A system for performing autonomous and semi-autonomous surgical procedures with a surgical laser, the system comprising:
a surgical robot configured to perform a surgical procedure on a patient, the surgical robot including:
a robotic arm;
a laser that is attached to the robotic arm and configured to emit a surgical laser beam based on one or more laser settings;
at least one imaging device that is configured to continuously capture image data of a surgical area of the patient; and
at least one sensor that is configured to continuously capture sensor data of at least one of the surgical robot and the patient; and
a surgical computing system in communication with the surgical robot, wherein the surgical computing system is configured to, before the surgical procedure:
retrieve, from a data store, at least one of historic patient data and historic surgical procedure data;
determine, based on the retrieved data, a pre-operative plan, wherein the pre-operative plan includes initial laser settings for the laser; and
transmit, to the surgical robot, the pre-operative plan, wherein the laser adjusts the one or more laser settings to the initial laser settings in response the surgical robot receiving the pre-operative plan; and wherein the surgical computing system is configured to, during the surgical procedure:
continuously receive, from the at least one imaging device and the at least one sensor, the image data and the sensor data;
determine, based on the received data, at least one adjustment to the initial laser settings; and
transmit, to the surgical robot, the at least one adjustment to the initial laser settings, wherein the laser automatically adjusts the one or more laser settings based on the at least one adjustment during the surgical procedure, wherein the surgical computing system is further configured to determine the initial laser settings based on:
polling a data store for configurations of the surgical robot for a same surgical procedure as the surgical procedure;
determining an initial position of the robotic arm based on (i) at least one of the configurations of the surgical robot and (ii) the retrieved data;
determining workflow parameters for the surgical robot during the surgical procedure based on the retrieved data; and
transmitting the initial position of the robotic arm and the workflow parameters to the surgical robot to cause the surgical robot to automatically adjust one or more settings before the surgical procedure.

20. The system of claim 19, wherein the surgical computing system is configured to determine, during the surgical procedure, at least one adjustment to the initial laser settings based on:
identifying a treatment area in the image data based on mapping the surgical area that is captured in the image data;
determining a quantity of treated tissue in the identified treatment area; and
determining, based on the quantity of treated tissue, the at least one adjustment to the initial laser settings.

21. The system of claim 19, wherein the surgical computing system is configured to determine that the surgical procedure is complete based on:
identifying a treatment area in the image data based on mapping the surgical area that is captured in the image data;
determining a quantity of treated tissue in the identified treatment area; and
determining that the quantity of treated tissue exceeds a threshold value.

22. A surgical laser of a surgical robot that is used for performing autonomous and semi-autonomous surgical procedures, the surgical laser being configured to:
receive, from a surgical computing system in communication with the surgical robot and before a surgical procedure, initial laser settings for the laser, wherein the initial laser settings were determined, by the surgical computing system, as part of a pre-operative plan for the surgical procedure based on at least one of historic patient data and historic surgical procedure data;
automatically adjust, before the surgical procedure, one or more laser settings to the initial laser settings;
perform the surgical procedure based on the adjusted one or more laser settings;
receive, from the surgical computing system and during the surgical procedure, at least one adjustment to the initial laser settings; and automatically adjust, during the procedure, the one or more laser settings based on the at least one adjustment received during the surgical procedure, wherein the surgical laser is attached to a robotic arm of a surgical robot and configured to emit a surgical laser beam during the surgical procedure and based on the one or more laser settings, wherein the surgical computing system is further configured to determine the initial laser settings based on:
polling a data store for configurations of the surgical robot for a same surgical procedure as the surgical procedure;
determining an initial position of the robotic arm based on (i) at least one of the configurations of the surgical robot and (ii) the retrieved data;
determining workflow parameters for the surgical robot during the surgical procedure based on the retrieved data; and
transmitting the initial position of the robotic arm and the workflow parameters to the surgical robot to cause the surgical robot to automatically adjust one or more settings before the surgical procedure.

23. The surgical laser of claim 22, wherein the surgical laser receives the at least one adjustment, from the surgical computing system and during the surgical procedure, based on a determination, by the surgical computing system, that the surgical laser is within a threshold distance from a boundary of a surgical area of a patient during the surgical procedure, wherein the at least one adjustment includes rotating the surgical laser a predetermined amount of degrees such that the surgical laser is oriented away from the boundary of the surgical area.

24. The surgical laser of claim 22, wherein the surgical laser is configured to:
temporarily stop performing the surgical procedure as the surgical laser automatically adjusts the one or more laser settings; and
resume performing the surgical procedure once the surgical laser completes automatically adjusting the one or more laser settings.

* * * * *